(12) United States Patent
O'Mahony

(10) Patent No.: US 9,808,567 B2
(45) Date of Patent: Nov. 7, 2017

(54) DIAPHRAGM REPOSITIONING FOR PRESSURE POD USING POSITION SENSING

(71) Applicant: GAMBRO LUNDIA AB, Lund (SE)

(72) Inventor: John O'Mahony, Maple Grove, MN (US)

(73) Assignee: Gambro Lundia AB, Lund (SE)

( * ) Notice: Subject to any disclaimer, the term of this patent is extended or adjusted under 35 U.S.C. 154(b) by 330 days.

(21) Appl. No.: 14/649,612

(22) PCT Filed: Dec. 13, 2013

(86) PCT No.: PCT/US2013/075057
§ 371 (c)(1),
(2) Date: Jun. 4, 2015

(87) PCT Pub. No.: WO2014/093846
PCT Pub. Date: Jun. 19, 2014

(65) Prior Publication Data
US 2015/0314058 A1 Nov. 5, 2015

Related U.S. Application Data

(60) Provisional application No. 61/737,264, filed on Dec. 14, 2012.

(51) Int. Cl.
*G01L 7/08* (2006.01)
*A61M 1/36* (2006.01)
(Continued)

(52) U.S. Cl.
CPC ........ *A61M 1/3639* (2013.01); *A61M 1/3641* (2014.02); *F04B 45/0536* (2013.01);
(Continued)

(58) Field of Classification Search
None
See application file for complete search history.

(56) References Cited

U.S. PATENT DOCUMENTS 4,226,124 A 10/1980 Kersten
4,227,420 A 10/1980 Lamadrid
(Continued)

FOREIGN PATENT DOCUMENTS

CN 1739014 2/2006
CN 101398336 4/2009
(Continued)

OTHER PUBLICATIONS

PCT International Search Report and Written Opinion for PCT/US2013/075057 dated Mar. 13, 2014 (12 pages).
(Continued)

*Primary Examiner* — Andre Allen
(74) *Attorney, Agent, or Firm* — Mueting, Raasch & Gebhardt, P.A.

(57) ABSTRACT

Pressure measurement system (e.g., for an extracorporeal treatment system), method and pressure pod apparatus including a position sensor for use in repositioning a diaphragm that separates a liquid side cavity from a transducer side cavity (e.g., operatively connected to a pressure transducer); the liquid side cavity being in fluid communication with an inlet and an outlet.

20 Claims, 17 Drawing Sheets

(51) Int. Cl.
  *F04B 45/053* (2006.01)
  *F04B 49/00* (2006.01)
  *G01B 11/14* (2006.01)
  *G01B 7/00* (2006.01)
  *G01L 19/00* (2006.01)
  *G01L 11/00* (2006.01)
  *G01L 19/14* (2006.01)

(52) U.S. Cl.
  CPC ............ *F04B 49/002* (2013.01); *G01B 7/003* (2013.01); *G01B 11/14* (2013.01); *G01L 7/088* (2013.01); *G01L 11/004* (2013.01); *G01L 19/0023* (2013.01); *G01L 19/0038* (2013.01); *G01L 19/0046* (2013.01); *G01L 19/144* (2013.01); *A61M 2205/3331* (2013.01)

(56) References Cited

U.S. PATENT DOCUMENTS

| | | | |
|---|---|---|---|
| 4,321,578 A | 3/1982 | Nagasu | |
| 4,625,560 A * | 12/1986 | Sanders | G01L 9/0073 331/65 |
| 4,666,598 A | 5/1987 | Heath | |
| 4,712,566 A | 12/1987 | Hök | |
| 4,886,070 A | 12/1989 | Demarest | |
| 4,909,083 A | 3/1990 | Fazeli | |
| 4,970,900 A | 11/1990 | Shepherd | |
| 5,441,636 A | 8/1995 | Chevallet | |
| 5,483,994 A | 1/1996 | Maurer | |
| 5,551,300 A | 9/1996 | Vurek | |
| 5,679,245 A | 10/1997 | Manica | |
| 5,722,399 A | 3/1998 | Chevallet | |
| 5,762,805 A | 6/1998 | Truitt | |
| 5,776,345 A | 7/1998 | Truitt | |
| 5,798,462 A * | 8/1998 | Briefer | G01D 5/202 73/722 |
| 5,910,252 A | 6/1999 | Truitt | |
| 6,040,903 A | 3/2000 | Lysen | |
| 6,122,972 A | 9/2000 | Crider | |
| 6,526,357 B1 | 2/2003 | Soussan | |
| 6,542,761 B1 | 4/2003 | Jahn | |
| 6,595,943 B1 | 7/2003 | Burbank | |
| 6,684,710 B2 | 2/2004 | Chevallet | |
| 6,821,432 B2 | 11/2004 | Metzner | |
| 6,895,130 B1 | 5/2005 | Mengle | |
| 7,107,837 B2 | 9/2006 | Lauman | |
| 7,147,613 B2 | 12/2006 | Burbank | |
| 7,153,286 B2 | 12/2006 | Busby | |
| 7,272,976 B2 | 9/2007 | Gajdeczko | |
| 7,284,443 B2 | 10/2007 | Sato | |
| 7,530,276 B2 | 5/2009 | Sato | |
| 7,771,380 B2 | 8/2010 | Jönsson | |
| 7,780,618 B2 | 8/2010 | Felt | |
| 7,803,628 B2 | 9/2010 | Glocker | |
| 8,054,452 B2 | 11/2011 | Bado | |
| 8,269,953 B2 | 9/2012 | Bado | |
| 8,333,724 B2 | 12/2012 | Barrett | |
| 8,743,353 B2 | 6/2014 | Bado | |
| 8,743,354 B2 | 6/2014 | Barrett | |
| 2003/0136189 A1 | 7/2003 | Lauman | |
| 2004/0144724 A1 | 7/2004 | Bosetto | |
| 2007/0000333 A1 | 1/2007 | Brugger | |
| 2007/0179433 A1 | 8/2007 | Jonsson | |
| 2009/0101566 A1 | 4/2009 | Crnkovich | |
| 2010/0206784 A1 | 8/2010 | Weaver | |
| 2012/0062869 A1 | 3/2012 | Bado | |
| 2012/0125116 A1 * | 5/2012 | Weisser | G01L 9/007 73/728 |
| 2012/0218541 A1 | 8/2012 | Barrett | |
| 2012/0232411 A1 * | 9/2012 | Brunner | A61B 5/0876 600/485 |
| 2013/0291646 A1 * | 11/2013 | Weisser | G01L 9/007 73/756 |
| 2015/0226625 A1 * | 8/2015 | Jacob | G01L 9/12 73/718 |
| 2015/0306299 A1 * | 10/2015 | Stuva | A61M 1/3639 604/121 |

FOREIGN PATENT DOCUMENTS

| | | |
|---|---|---|
| DE | 202004020869 | 3/2006 |
| DE | 202013011936 | 12/2014 |
| EP | 0291727 | 11/1992 |
| EP | 0392897 | 12/1993 |
| EP | 1078642 | 2/2001 |
| EP | 1213033 | 2/2007 |
| EP | 2233164 | 9/2010 |
| EP | 1728526 | 12/2012 |
| EP | 2461844 | 12/2013 |
| GB | 2176595 | 12/1986 |
| WO | WO 96/40321 | 12/1996 |
| WO | WO 01/37899 | 5/2001 |
| WO | WO 02/098492 | 12/2002 |
| WO | WO 2004/061399 | 7/2004 |
| WO | WO 2012/033738 | 3/2012 |
| WO | WO 2012/033753 | 3/2012 |
| WO | WO 2012/116336 | 8/2012 |
| WO | WO 2014/093846 | 6/2014 |

OTHER PUBLICATIONS

PCT International Preliminary Examination Report for PCT/US2013/075057 dated Jun. 25, 2015 (9 pages).

* cited by examiner

DIAPHRAGM REPOSITIONING FOR PRESSURE POD USING POSITION SENSING

This application is the U.S. National Stage Application of International Application No. PCT/US2013/075057, filed Dec. 13, 2013 and published in English on Jun. 19, 2014 as International Publication No. WO 2014/093846 A1, which claims the benefit under 35 U.S.C. 119(e) of U.S. Provisional Application No. 61/737,264 filed Dec. 14, 2012; all of which are incorporated herein by reference in their entirety.

BACKGROUND

The disclosure herein relates to pressure pods, e.g., for use in measuring pressure of a liquid flowing through the pod. For example, such pressure pods may be used for measurement of pressure in extracorporeal blood sets.

Extracorporeal blood sets, for example, are used in a variety of medical procedures to treat patients with the infusion of drugs, dialysis, continuous renal replacement therapy (CRRT), extracorporeal membrane oxygenation (ECMO), etc. Reducing cost while maintaining safety and accuracy are of concern in today's healthcare environment. Minimizing the amount of time that a user has to interface with the medical device, e.g., by removing repetitive tasks, reduces the cost of operation and frees the user's time to increase the quality of health care.

In many extracorporeal blood sets (e.g., disposable blood sets) provided, for example, for use in therapy systems, pressure pods are used to separate the liquid/blood filled disposable extracorporeal circuit from an electronic pressure sensor of the system by preventing liquid ingress and contamination while enabling the transfer and measurement of pressure. Such pressure pods may typically include a pressure transducer side separated from a liquid flow side by a diaphragm. In one or more configurations, for example, the pressure transducer side of the pressure pod is filled with air in a sealed space providing isolation (e.g., electrical isolation) thereof from the liquid flow side (e.g., through which liquid may flow) and a medium for the transfer of pressure from the liquid flow side to the pressure transducer side of the pressure pod, e.g., the compression of air. For example, the diaphragm which separates the pressure transducer side from the liquid flow side of the pressure pod may be flexible and oversized to ensure none of the force exerted by the pressure on the diaphragm in the extracorporeal blood circuit is lost to the tension or compression of the diaphragm. Further, for example, the pressure pod (e.g., the pressure transducer side of the pressure pod) may be operatively connected by tubing (e.g., air filled) to a pressure transducer for sensing pressure at a distance away from the pressure pod (e.g., a pressure transducer located in a system housing upon which the extracorporeal blood set is mounted).

Since air is compressible and follows the ideal gas law under low pressures which exist in the extracorporeal blood circuit, the diaphragm position is a function, for example, of the atmospheric pressure, the volume of air in the closed space encompassing the air volume of the pressure transducer, any tubing volume between the pressure transducer and pressure pod, the elasticity of the tubing, and the volume of air in the pressure pod. As the circuit pressure increases and decreases in the liquid path during therapy such as dialysis, the position of the diaphragm will change accordingly. For example, under negative pressure the flexible membrane, e.g., the diaphragm, will deflect towards the blood portion, e.g., liquid flow side, of the pressure pod and, for example, during positive pressure, the flexible membrane will flex toward the air side or pressure transducer side of the pressure pod.

However, if there is too little or too much air volume in the pressure transducer side, i.e., the air side, of the pressure pod due to, for example, a leak, a change in temperature, a change in blood pressure, or a change in atmospheric pressure, the potential exists for the flexible diaphragm to touch the pod casing on the liquid flow side of the pressure pod (e.g., topped out) or come under tension (e.g., due to the slack in the flexible diaphragm being used) and bottom out (e.g., touch the pod casing on the transducer side of the pressure pod) resulting in an incorrect pressure reading because the true circuit pressure is no longer being transmitted. Conventionally, medical device systems have overcome such limitations by, for example, alerting the user to changes in pressure or at set periods of time to request the user to check the diaphragm position and/or to enable a repositioning of the diaphragm by the user as further described herein. Such a check and/or reposition procedure takes user time and also may momentarily disable pressure measurement during the procedure (e.g., during therapy being provided to a patient).

For example, during a software initiated periodic check and/or reposition procedure carried out by a user, the diaphragm position may be adjusted back to a centered measuring position by infusing air to or withdrawing air from the enclosed space on the transducer side of the pressure pod. The trapped volume of air within the pressure pod is a known volume and by flexing the diaphragm under positive and negative pressure, the extension limits of the flexible diaphragm may be found by examining the rate of the change in pressure. For example, when the diaphragm deflection is halted due to tension or due to the diaphragm coming into contact with the sides of the pod (e.g., topped out or bottomed out on the pod casing), the rate of change of pressure will dramatically increase because the compliance of the chamber decreases, where compliance is measured in terms of pressure change per change in volume of air. Once both the positive and negative extension limits are determined, the centered measuring position may be found by infusing a known volume of air into the closed system (e.g., by activating a valve and connecting a positive displacement air pump to the enclosed space on the transducer side of the pressure pod).

In other words, for example, a disposable extracorporeal blood set connectable to a therapy system (e.g., mounted on a system housing and connected to one or more pressure transducers therein), may contain multiple circular pressure pods. Each pressure pod may contain a diaphragm that separates a liquid (e.g. blood in the liquid side of the pressure pod) from an air cavity (e.g., on the transducer side of the pressure pod) and which is configured to fit into a pressure sensor housing on a control unit (e.g., a connection apparatus for mounting the pressure pod on a dialysis unit). The pressure pods and pressure transducers (e.g., inside the control unit, such as a dialysis unit) enable noninvasive pressure monitoring of the liquid (e.g., blood), since the liquid never comes into contact with the actual pressure transducer. However, for the sensor to yield valid pressure readings, the pressure pod diaphragm must stay in the center range of the pressure pod. This may be accomplished by using an air pump (e.g., of a pump system) to add air to or remove air from the pressure pod air cavity (e.g., on the transducer side of the pressure pod) such that the air pressure on the air side of the diaphragm (e.g., the transducer side of the pressure pod) is equal to the liquid pressure on the other side of the diaphragm (e.g., the liquid flow side of the pressure pod). This may be referred to as having the pod diaphragm "in the measuring position."

Current technology generally, for example, uses two methods to move the diaphragm to the centered position. For example, an Open Loop Diaphragm Repositioning Sequence may be used. Such a sequence may be performed as follows. Periodically, an air pump may be operated to either add or remove air such that the pressure transducer readings from a given pressure pod is increased or decreased by 100 mmHg. If the initial pressure difference between the air cavity pressure and liquid pressure is small, then the diaphragm should be pushed against one of the pressure pod walls (e.g., on the transducer side or the liquid flow side of the pressure pod). This is referred to as the diaphragm either bottomed out (e.g., minimum air cavity volume) or topped out (e.g., maximum air cavity volume). Then the pump may be operated to add or remove air volume equal to ½ the total volume of the pod. If the diaphragm was either bottomed out or topped out, this should center the diaphragm in the pod. However, if the diaphragm was not actually bottomed out or topped out, then it will not be centered after the open loop diaphragm repositioning sequence. Numerous conditional checks (e.g., such as calculating the derivative of the pressure readings while the pump is adding or removing air) are done to determine success or failure of the open loop repositioning sequence. If these checks indicate a failure, then a Research of Plateau Test Sequence may be executed. If the checks indicate success, then the repositioning sequence for the given pod may be terminated.

The Research of Plateau Repositioning Sequence may be performed as follows. This sequence may be executed if automated checks indicate that the open loop diaphragm repositioning sequence failed. In this sequence, the air pump is again used to add/remove air to/from the pod air cavity (e.g., on the transducer side of the pressure pod). In this case, however, the derivative of the pressure transducer reading is calculated while the pump is adding/removing air at a constant rate. If the diaphragm is in the measuring range, then the pressure derivative magnitude will be small. When the diaphragm reaches either a bottomed out or topped out condition, however, the pressure derivative magnitude increases beyond a threshold, indicating that the diaphragm has reached one wall of the pressure pod. At that point, the pump direction may be reversed and continue to operate until the pressure derivative again exceeds a threshold indicating that the diaphragm has contacted the opposite wall of the pressure pod. The air pump may again be reversed to add or remove an air volume equal to half of the volume required to move the diaphragm from the initial pod wall contact to the opposite pod wall contact. The diaphragm should then be centered in the pod and pressure readings from the pressure sensor (e.g., pressure measurements) should be valid.

Further, for example, the position of the diaphragm may also be manually repositioned by a user. For example, based upon the user visually examining the position of the diaphragm, the user may infuse air or remove air from the system to center the diaphragm (e.g., the user may control the pump to infuse or remove air). However, as mentioned herein, such processes (for example, at set periods of time requesting the user to check the diaphragm position) undesirably take user time.

SUMMARY

The present disclosure describes systems, methods, and apparatus which addresses the need for a user to check and/or reposition the diaphragm to a central measuring position during system operation (e.g., the need for the user to periodically reposition the diaphragm and to interface with the device due to changes in circuit pressure or changes in environmental conditions, such as temperature and barometric pressure). The present disclosure describes systems, methods, and apparatus usable for ensuring that the flexible membrane (e.g., flexible diaphragm) used in a pressure pod is kept in a central measuring position during system operation. For example, in one or more embodiments, the present disclosure describes systems, methods, and apparatus for use in setting the diaphragm position automatically based upon sensed diaphragm position and using the sensed diaphragm position in a feedback loop to address the need for a user to perform the task periodically. As such, one or more embodiments disclosed herein may reduce therapy interruptions (e.g., allowing the repositioning task to be carried out on a much more frequent basis while minimizing disruption time in the system by, for example, removing the need for the diaphragm to be periodically fully deflected in the determination of extension limits).

A pressure measurement system according to one or more embodiments of the present disclosure includes a pressure pod body including at least a pod body portion and a base body portion, and a diaphragm separating a liquid side cavity defined at least in part by the pod body portion from a transducer side cavity defined at least in part by the base body portion. The liquid side cavity is in fluid communication with an inlet and an outlet, and the diaphragm is displaceable from a centered measuring position into the liquid side cavity towards the pod body portion and is displaceable from the centered measuring position into the transducer side cavity towards the base body portion. The system further includes a pressure transducer operatively coupled to the transducer side cavity such that pressure of liquid when present in the liquid side cavity is transferred to the transducer side cavity via the diaphragm and measureable by the pressure transducer and a position sensor to sense the position of the diaphragm. Still further, the system includes a controller operatively coupled to the position sensor to receive one or more signals representative of the position of the diaphragm and to generate a control signal based thereon for use in repositioning the diaphragm towards the centered measuring position and pump apparatus operatively coupled to the controller and the transducer side cavity to reposition the diaphragm to the centered measuring position based on the control signal generated by the controller.

One or more embodiments of the system may include one or more of the following: the position sensor may include at least one of an electro-optical proximity sensor and a capacitive proximity sensor; a system housing to contain at least the controller and the pressure transducer and a connection apparatus to mount the pressure pod body on the system housing (e.g., the connection apparatus may include a port to connect the transducer side cavity to the pressure transducer contained in the system housing when the pressure pod body is mounted on the system housing by the connection apparatus); the position sensor may include a proximity sensor located to sense the position of the diaphragm when the pressure pod body is mounted on a system housing by connection apparatus; the proximity sensor may include an electro-optical proximity sensor including at least an optical transmitter device and an optical detector device mounted on the connection apparatus to sense the position of the diaphragm when the pressure pod body is mounted on a system housing by connection apparatus; the proximity sensor may include a capacitive proximity sensor including one or more electrodes located adjacent the base body portion of the pressure pod body when the pressure pod body is mounted on a system housing by connection apparatus (e.g., the one or more electrodes may be separated from the base body portion by a high dielectric material, the capacitive proximity sensor may include an electrode pad that may be entirely separated from the base body portion by the high dielectric material, the capacitive proximity sensor may include an electrode pad such that the electrode pad and the diaphragm lie along an axis of the pressure pod body and the cross-sectional area of the electrode pad orthogonal to the axis is substantially the same as the cross-sectional area of the diaphragm orthogonal to the axis, the capacitive proximity sensor may include one or more electrodes coupled to at least a portion of the base body portion, or the proximity sensor may include a capacitive proximity sensor including one or more electrodes provided proximate an end of a port located adjacent or within the transducer side cavity when the pressure pod is mounted on a system housing).

A pressure measurement method according to one or more embodiments may include providing a pressure pod body that includes at least a pod body portion and a base body portion and a diaphragm that separates a liquid side cavity defined at least in part by the pod body portion from a transducer side cavity defined at least in part by the base body portion (e.g., wherein the liquid side cavity is in fluid communication with an inlet and an outlet, and further wherein the diaphragm is displaceable from a centered measuring position into the liquid side cavity towards the pod body portion and is displaceable from the centered measuring position into the transducer side cavity towards the base body portion). The method may further include sensing pressure of a liquid in the liquid side cavity between the inlet and the outlet, wherein the pressure of liquid when present in the liquid side cavity is transferred to the transducer side cavity via the diaphragm; sensing the position of the diaphragm; generating a control signal based on the sensed position of the diaphragm; and repositioning the diaphragm towards the centered measuring position based on the control signal.

In one or more embodiments of the method, generating a control signal based on the sensed position of the diaphragm may include setting a predetermined range of acceptable diaphragm positions for sensing pressure; comparing the sensed position of the diaphragm to the predetermined range; and generating a control signal based on the comparison.

One or more embodiments of the method may include one or more of the following: sensing the position of the diaphragm by sensing the position of the diaphragm at multiple times over multiple rotations of a pump providing for flow of the liquid through the liquid side cavity from inlet to outlet and averaging the sensed position of the diaphragm at the multiple times; repositioning the diaphragm towards the centered measuring position by providing air to or removing air from the transducer side cavity; sensing the position of the diaphragm by using a proximity sensor to sense the position of the diaphragm (e.g., the proximity sensor may include at least one of an electro-optical proximity sensor and a capacitive proximity sensor described herein).

Further, in one or more embodiments of the method, the method may further include providing a system housing to contain at least a controller to generate the control signal and a pressure transducer to sense pressure of the liquid in the liquid side cavity; providing a connection apparatus to mount the pressure pod body on the system housing (e.g., wherein the connection apparatus may include a port to connect the transducer side cavity to the pressure transducer contained in the system housing when the pressure pod body is mounted on the system housing by the connection apparatus); mounting the pressure pod body on the system housing; and using a proximity sensor to sense the position of the diaphragm when the pressure pod body is mounted on the system housing by the connection apparatus.

One or more embodiments of a pressure measurement apparatus to be operatively mounted by a connection apparatus on a system housing (e.g., a system housing that contains a pressure transducer therein) may include a pressure pod body configured to be mounted on the system housing by the connection apparatus. For example, the pressure pod body may include at least a pod body portion and a base body portion. A diaphragm may separate a liquid side cavity defined at least in part by the pod body portion from a transducer side cavity defined at least in part by the base body portion (e.g., wherein the liquid side cavity is in fluid communication with an inlet and an outlet, wherein the transducer side cavity is connectable to the pressure transducer such that pressure of liquid when present in the liquid side cavity is transferred to the transducer side cavity via the diaphragm and measureable by the pressure transducer, and further wherein the diaphragm is displaceable from a centered measuring position into the liquid side cavity towards the pod body portion and is displaceable from the centered measuring position into the transducer side cavity towards the base body portion). Further, the pressure measurement apparatus may include a position sensor positioned adjacent the base body portion usable to sense the position of the diaphragm (e.g., the position sensor may include a proximity sensor such as described herein).

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

DETAILED DESCRIPTION OF EXEMPLARY EMBODIMENTS

Figure 1:
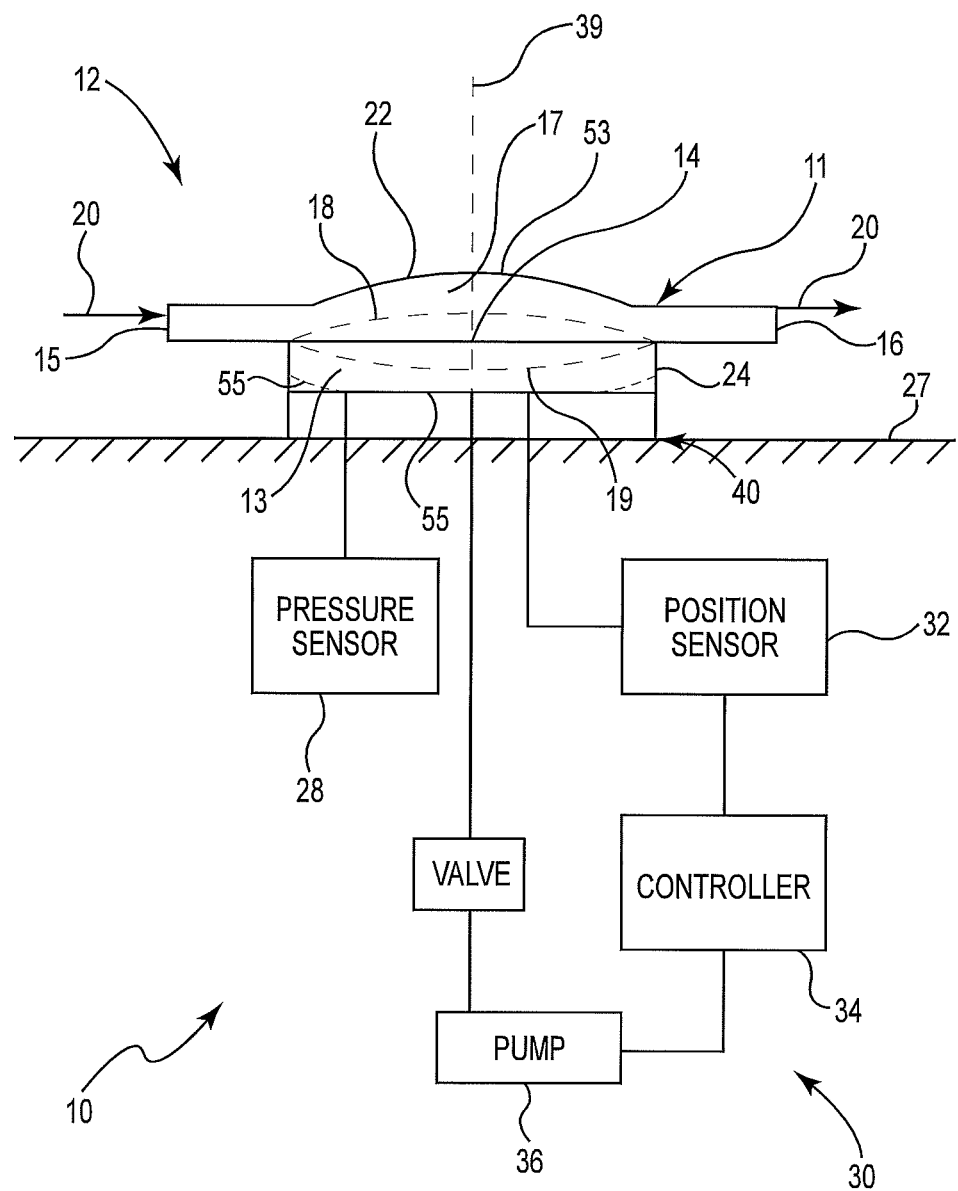
FIG. 1 is a generalized illustration of an exemplary pressure measurement system including a pressure pod apparatus and diaphragm repositioning system.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems, methods, and apparatus for use in the repositioning of a diaphragm in a pressure pod apparatus shall be described with reference to FIGS. 1-12. For example, such systems, apparatus, and methods may sense or measure the position of a pressure pod diaphragm using a sensor to detect the distance between the diaphragm and the sensor (e.g., a reference point) and to keep this distance within a predetermined distance range (e.g., a centered measuring position). Further, for example, such systems, methods, and apparatus may measure the position of the diaphragm using a non-contact sensor (e.g., a proximity sensor).

FIG. 1 shows one general exemplary embodiment of a pressure measurement system 10 including a pressure pod apparatus 12 for use in measuring the pressure of a flow of fluid therethrough (e.g., a flow of liquid, such as blood, shown generally by arrows 20). The pressure pod apparatus 12 includes a pressure pod body 11 including at least a pod body portion 22 and a base body portion 24 that may be coupled to a connection apparatus 40 (e.g., a base body portion 24 that may be coupled to a mating receptacle) for use in, for example, mounting the pressure pod apparatus 12 relative to a system housing 27 and/or for use in connecting the pressure pod apparatus 12 to components within the system housing 27.

As shown in the exemplary embodiment of FIG. 1, a diaphragm 14 (e.g., also referred to herein as a flexible membrane) separates a liquid side cavity 17 defined at least in part by the pod body portion 22 from a transducer side cavity 13 (e.g., an air cavity) defined at least in part by the base body portion 24. The liquid side cavity 17 is in fluid communication with an inlet 15 and an outlet 16 (e.g., through which a liquid may flow as indicated by arrows 20). The diaphragm 14 is displaceable from a centered measuring position into the liquid side cavity 17 towards the pod body portion 22 as shown by dashed line 18 and is displaceable from the centered measuring position into the transducer side cavity 13 towards the base body portion 24 as shown by dashed line 19. The centered measuring position may be primarily defined as the neutral state of the diaphragm when no forces are applied thereto, or otherwise definable as the state of the diaphragm when the pressure on the transducer side of the diaphragm is equal to the pressure on the liquid flow side of the diaphragm. At least in one embodiment, the centered measuring position is generally a range of centered diaphragm positions acceptable for accurate pressure measurement (e.g., a range of positions where the diaphragm is flexible and transfers pressure accurately; as opposed to the diaphragm being taut such that pressure transferred is a function of both the elasticity of the diaphragm as well as the liquid pressure on the diaphragm). A pressure transducer 28 may be operatively coupled (e.g., by one or more tubes with or without use of the connection apparatus 40) to the transducer side cavity 13 such that pressure of liquid (e.g., liquid flow designated by arrows 20) when present in the liquid side cavity 17 is transferred to the transducer side cavity 13 via the diaphragm 14 and measureable by the pressure transducer 28.

The pressure measurement system 10 further includes a diaphragm repositioning system 30 operatively coupled to automatically (e.g., without user manual intervention such as the check and/or reposition process described in the Background herein) reposition the diaphragm 14 towards the centered measuring position. The diaphragm repositioning system 30 includes a position sensor 32 (e.g., a proximity sensor such as an electro-optical, inductive, ultrasonic, linear variable displacement transformer (LCDT), or capacitive proximity sensor) to sense the position of the diaphragm 14. The diaphragm repositioning system 30 further includes a controller 34 operatively coupled to the position sensor 32 to receive one or more signals representative of the position of the diaphragm 14 and to generate a control signal based thereon for use in repositioning the diaphragm 14 towards the centered measuring position. A pump apparatus 36 of the diaphragm repositioning system 30 is operatively coupled (e.g., by one or more tubes, sensors, feedback loops, valves, etc.) to the controller 34 and the transducer side cavity 13 to reposition the diaphragm 14 towards the centered measuring position based on the control signal generated by the controller 34. For example, air may be provided to or removed from the transducer side cavity 13 by way of a valve apparatus (e.g., 2/2 way valve, such as a solenoid valve) connected between the air pump apparatus 36 and the transducer side cavity 13 by at least tubing.

The position sensor 32 may be any position sensor suitable to provide information regarding the position of diaphragm 14. For example, the position sensor 32 may be a non-contact sensor for measuring the position of the diaphragm 14 such as a non-contact proximity sensor (e.g., an electro-optical proximity sensor, a capacitive proximity sensor, an inductive proximity sensor, etc.) or any other type of non-contact position sensor such as a reflective sensor, ultrasonic sensor, etc., suitable for measuring the position of the diaphragm (e.g., measuring the position of one or more regions of the diaphragm, one or more points on the diaphragm, one or more points or regions centered about the axis 39, etc.). Further, for example, direct contact type sensors may also be used. However, such sensors may need to be complimented with error correction techniques to correct for forces being exerted by the sensor on the diaphragm 14.

The position sensor 32 may include or be provided by any number of components suitable to provide position sensing and such components may be positioned at different locations or form a part of various components of the pressure measurement system 10. For example, the position sensor may include use of an optical transmitter device and an optical detector device (e.g., as part of an electro-optical proximity sensor) positioned with and/or included as a part of the connection apparatus 40 (see, for example, FIGS. 8A-8C). Further, for example, the position sensor may include use of one or more electrodes (e.g., an electrode pad as part of a capacitive proximity sensor) positioned with and/or forming a part of the connection apparatus 40 (see, for example, FIGS. 9 and 11). Further, for example, the position sensor may include use of one or more electrodes (e.g., an electrode pad as part of a capacitive proximity sensor) positioned with and/or forming a part of the pressure pod apparatus 12 (see, for example, FIG. 10). In other words, a variety of position sensors may be used to sense the position of the diaphragm 14 and such position sensors may be positioned with and/or form a part of any number of components of the pressure measurement system 10, or may be provided completely separate from such components.

The controller 34 operatively coupled to the position sensor 32 may be any hardware/software architecture configured to provide the desired functionality. For example, the controller may include circuitry for sampling diaphragm position measurements, processing apparatus and associated software for processing data (e.g., signals representative of the position of the diaphragm 14) output circuitry to generate a control signal for use in repositioning the diaphragm 14 towards the center position. As described herein with reference to FIGS. 2A-2B, for example, such controller functionality may be carried out by the apparatus 360 described therein.

Such processing apparatus, may be, for example, any fixed or mobile computer system (e.g., a personal computer or mini-computer associated with, for example, a fluid treatment or processing system, such as a dialysis system). The exact configuration of the computing apparatus is not limiting and essentially any device capable of providing suitable computing capabilities and control capabilities (e.g., control of the positioning of the diaphragm 14 towards or to the centered measuring position) may be used. Further, various peripheral devices, such as a computer display, mouse, keyboard, memory, printer, scanner, are contemplated to be used in combination with processing apparatus, and its associated data storage. For example, data storage may allow for access to processing programs or routines and one or more other types of data that may be employed to carry out the illustrative methods and functionality as described herein.

In one or more embodiments, the methods or systems described herein may be implemented using one or more computer programs or processes (or systems including such processes or programs) executed on programmable computers, such as computers that include, for example, processing capabilities, data storage (e.g., volatile or non-volatile memory and/or storage elements), input devices, and output devices. For example, the systems and methods described herein may be considered to include multiple processes or programs that may be implemented alone or in combination. Program code and/or logic described herein may be applied to input data to perform functionality described herein and generate desired output information. The output information may be applied as input to one or more other devices and/or processes as described herein or as would be applied in a known fashion. For example, processing programs or routines may include programs or routines for performing various algorithms, including standardization algorithms, comparison algorithms, or any other processing required to implement one or more embodiments described herein, such as those for performing averaging of measurement data, generation of control signals, etc.

Software or programs used to implement the functionality described herein may be provided using any programmable language, e.g., a high level procedural and/or object orientated programming language that is suitable for communicating with a processing apparatus. Any such programs may, for example, be stored on any suitable device, e.g., a storage media, readable by a general or special purpose program, computer or a processor apparatus for configuring and operating the computer when the suitable device is read for performing the procedures described herein. In other words, at least in one embodiment, the methods and systems described herein may be implemented using a computer readable storage medium, configured with a computer program, where the storage medium so configured causes the processing apparatus to operate in a specific and predefined manner to perform functions described herein.

Pump apparatus 36 may be of any suitable configuration (e.g., a configuration formed of one or more pumps, valves, and tubes) to accomplish the repositioning of the diaphragm 14 via the transducer side cavity 13 (e.g., remove air from or infuse air into cavity 13). Pressure transducer 28 may be operatively configured with respect to the transducer side cavity 13 (e.g., a configuration in the form of one or more pumps, valves, and tubes) to accomplish the function of sensing the pressure in the transducer side cavity 13. Further, for example, the configuration of pump apparatus 36 may include components, such as tubes or valves, used for operatively coupling pressure transducer 28 to the transducer side cavity 13.

The pressure measurement system 10 including the diaphragm repositioning system 30 may be used in any fluid processing systems that would benefit therefrom. For example, exemplary systems that may benefit from such a diaphragm repositioning system include systems, generally referred to as dialysis systems. The general term dialysis as used here includes hemodialysis, hemofiltration, hemodiafiltration, hemoperfusion, liver dialysis, and therapeutic plasma exchange (TPE), among other similar treatment procedures. In dialysis generally, blood is taken out of the body and exposed to a treatment device to separate substances therefrom and/or to add substances thereto, and is then returned to the body. Although an extracorporeal blood treatment system 310 capable of performing general dialysis (as defined above, including TPE) and using diaphragm repositioning shall be described herein with reference to FIGS. 2A-2B, other systems such as those for infusion of drugs, performance of continuous renal replacement therapy (CRRT), extracorporeal membrane oxygenation (ECMO), hemoperfusion, liver dialysis, apheresis, TPE, etc. may benefit from the systems, methods, and apparatus described herein for the repositioning of a diaphragm and the present disclosure is not limited to the specific fluid processing systems described herein.

Figure 2A:
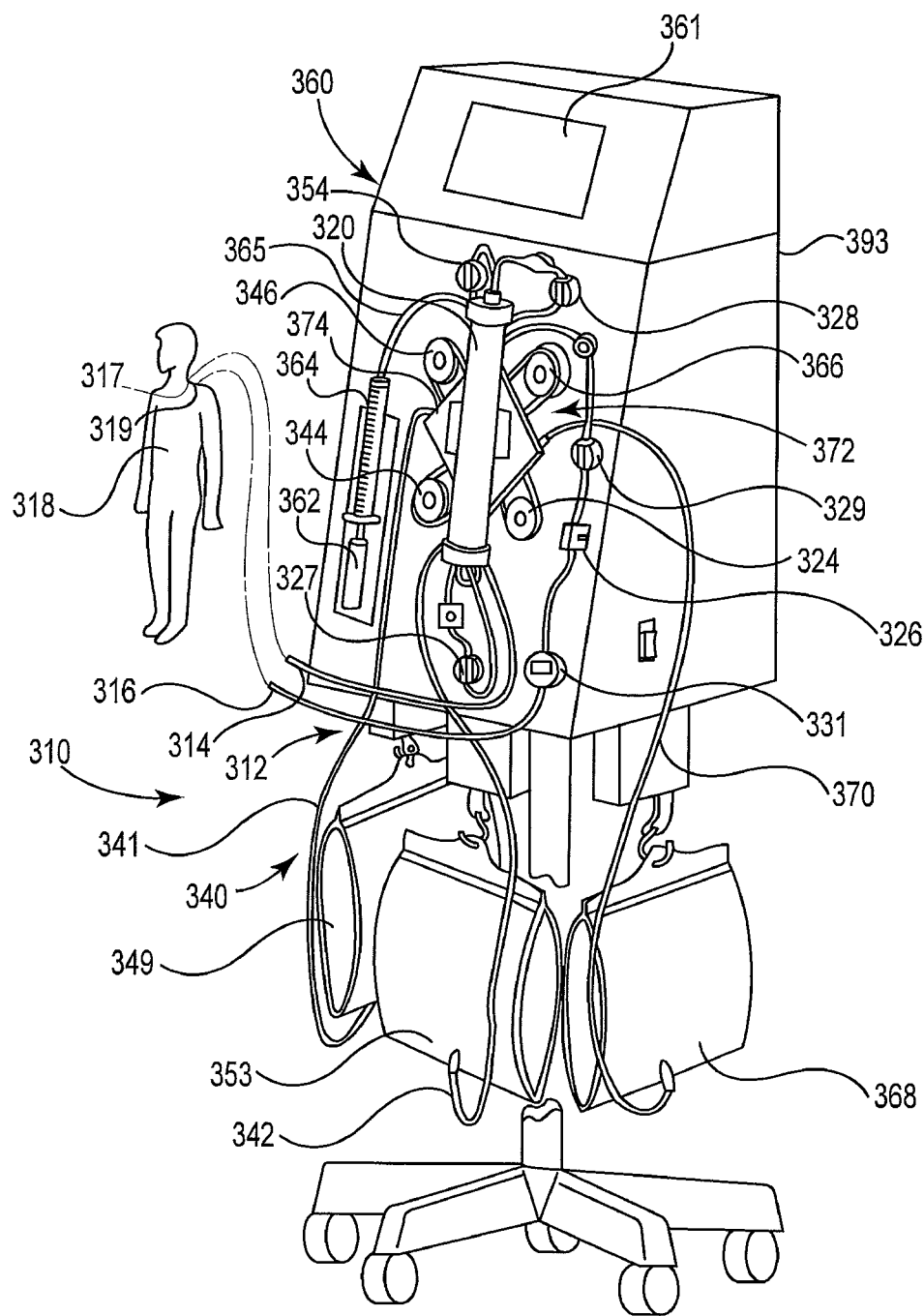
FIG. 2A is a perspective illustration of an exemplary fluid processing system that may include a pressure measurement system such as shown generally in FIG. 1.
Figure 2B:
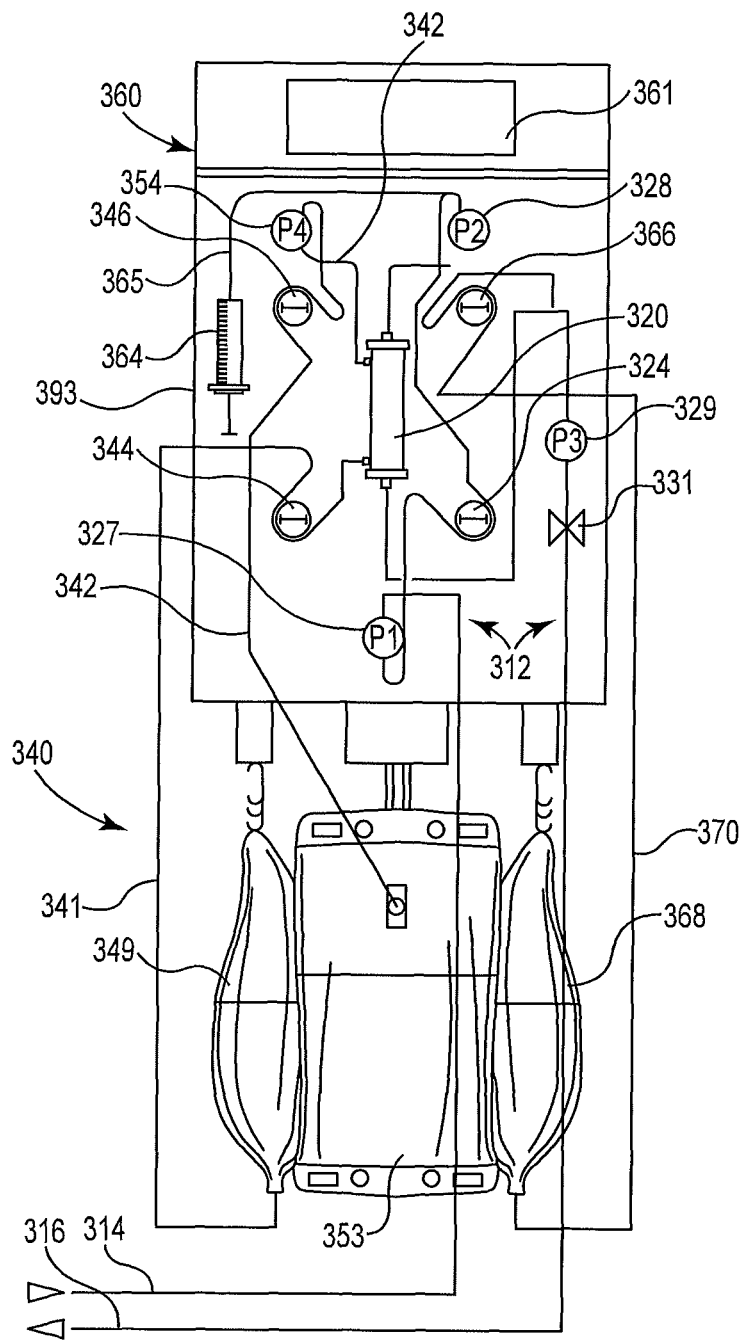
FIG. 2B is a front view of a portion of the exemplary fluid processing system shown in FIG. 2A.

In the perspective and partial front views of FIGS. 2A-2B, the exemplary extracorporeal blood treatment system 310 generally includes a blood tubing circuit 312 having first and second tubing segments 314 and 316 which are both connected to the vascular system of a patient 318 via access and return devices 317 and 319, respectively. Devices 317 and 319 may be cannulas, catheters, winged needles or the like as would be understood by one skilled in the art. Tubing segments 314 and 316 are also connected to a filtration or processing unit 320. In dialysis, filtration unit 320 is a dialyzer, which is also often referred to as a filter. In TPE, it may also be referred to as a plasma filter. In this exemplary system 310, a peristaltic pump 324 is disposed in operative association with the first tubing segment 314. Numerous other component devices of blood circuit 312 are also included as, for example, the three pressure sensors 327, 328, and 329, as well as the tubing clamp 331. Such pressure sensors 327, 328, and 329 may be configured as described herein such that diaphragms thereof may be automatically repositioned towards or to the centered measuring position therein, for example, during operation of system 310.

Also shown in FIGS. 2A-2B is the processing fluid or filtrate side of system 310 which generally includes a processing fluid circuit 340 having first and second processing fluid tubing segments 341 and 342. Each of these tubing segments is connected to the filtration unit 320. In these FIGS. 2A-2B, a respective fluid pump 344, 346 is operatively associated with each of these tubing segments 341 and 342. First tubing segment 341 is also connected to a processing fluid source (e.g., fluid bag 349) which may include electrolytes pre-mixed therein. Second tubing segment 342 is connected to a waste collection device (e.g., a waste container such as a bag 353). A pressure sensor 354 is also disposed in second dialysis fluid tubing segment 342 (e.g., pressure sensor 354 may be configured as described herein such that the diaphragm thereof may be automatically repositioned toward the centered measuring position, for example, during operation of system 310).

FIGS. 2A-2B show a system which is common as a basic model for numerous dialysis procedures including TPE. Additional fluid lines, circuits, and components may be added (or deleted) to increase treatment options. Further, as shown in FIGS. 2A-2B, the system 310 includes an extracorporeal blood control apparatus 360 which provides numerous treatment options which are controlled and/or monitored via the control/display screen 361 (e.g., a control apparatus or controller provided in a system housing 393). Touch-screen controls may be incorporated herewith and/or other conventional knobs or buttons (not shown) may be used. Other and more detailed information regarding an example apparatus 360 may be found in U.S. Pat. Nos. 5,679,245; 5,762,805; 5,776,345; and 5,910,252; inter alia.

A general dialysis treatment procedure as performed, for example, with an apparatus described with reference to FIGS. 2A-2B will be generally described for exemplary purposes. First, blood is removed from the patient 318 via access device 317 and flows through access line 314 to the filter 320. Filter 320 processes this blood according to a selected one or more of a number of extracorporeal blood treatment protocols (e.g., selected and controlled via screen interface 361 of control apparatus 360) and then return the processed or treated blood to the patient 318 through return line 316 and return device 319 inserted in or otherwise connected to the vascular system of the patient 318. The blood flow path to and from the patient 318, which includes the access device 317, the access line 314, the filter 320, as well as the return line 316 and return device 319 back to the patient forms the blood flow circuit 312.

Each of the treatment protocols used or carried out by apparatus 360 preferably involves passing the blood in the blood circuit 312 through filtration unit 320. The filtration unit 320 may use a conventional semi-permeable membrane (not specifically shown) to confine the blood in the primary circuit 312 to a primary chamber thereof and allows matter or molecules from the blood to migrate (by diffusion or convection) across the semi-permeable membrane into a secondary chamber, and generally may also allow matter or molecules from the secondary chamber to diffuse across the semi-permeable membrane from the secondary chamber into the blood in the primary chamber. Each treatment protocol may, therefore, generally involve removing extracorporeally undesired matter from the blood and/or adding extracorporeally desirable matter to the blood.

First pressure sensor 327 of the system 310 shown in FIGS. 2A-2B is connected in the access line 314 and allows the fluid pressure in the access line 314 to be monitored. The first peristaltic pump 324 is shown as operably connected to the access line 314 and controls the rate of blood flow through the blood circuit 312. Second pressure sensor 328 is connected in the blood circuit 312 between the first pump 324 and the blood entrance into the filter 320 and may be used to detect and monitor the pressure of the blood supplied to the entrance of the filter 320. The third pressure sensor 329 is connected at or near the outlet of the filter 320 and may be used to monitor the pressure of the blood in the return line 316 at the exit from the filter 320 for comparison with the pressure sensed by the sensor 328. The return clamp 331 connected in the blood circuit 312 selectively allows or terminates the flow of blood through the blood circuit 312 (e.g., return clamp 331 may be activated whenever air is detected in the blood by bubble detector 326). Further, a pump 362 may be connected to an anticoagulant container 364 to deliver anticoagulant through an anticoagulant line 365 to the blood in tubing segment 314 and a pump 366 may deliver replacement fluid from a replacement fluid container or bag 368 through a replacement fluid line 370.

The secondary flow circuit 340 is also shown in FIGS. 2A-2B as it interacts with filter 320. The secondary flow circuit 340 is connected to the secondary chamber of filter 320. Matter extracorporeally removed from the blood is removed from the secondary chamber of filter 320 through the outlet tubing segment 342 of the secondary flow circuit 340, and matter extracorporeally added to the blood is moved into filter 320 through inlet tubing segment 341 of the secondary flow circuit 340. The secondary flow circuit 340 generally includes the fluid source such as bag 349, inlet fluid line 341, third peristaltic pump 344, the secondary chamber of the filter 320, a waste fluid line 342, fourth pressure sensor 354, fourth pump 346, and the waste collection device such as container 353. The source fluid bag 349 contains a sterile processing fluid, generally isotonic to blood, into which blood impurities will diffuse through the semi-permeable membrane of the filtration unit 320. The pump 344 is connected in inlet fluid line 341 for delivering processing fluid from the processing fluid source 349 into an entrance to the filter 320. The waste collection container 353 is provided to collect or receive matter from the blood transferred across the semi-permeable membrane in filter 320 and/or to receive the used processing fluid after it has passed through the filter 320. The fourth pump 346 is connected to the waste collection line 342 for moving body fluid from the filter 320 into the waste collection container 353. The fourth pressure sensor 354 is also located in the waste collection line 342 for the purpose of monitoring the pressure in the secondary chamber of filter 320.

The filtration unit 320, the flow tubing lines, and the other components in the primary and secondary flow circuits 312 and 340 described herein (with the exception, for example, of the pumps and perhaps a few other items) may be formed as an integral, replaceable unit (e.g., an extracorporeal blood set). An example of such an integral replaceable unit is described in greater detail in U.S. Pat. No. 5,441,636 entitled Integrated Blood Treatment Fluid Module (see also, U.S. Pat. No. 5,679,245, entitled Retention Device for Extracorporeal Treatment Apparatus).

As can generally be appreciated from FIGS. 2A-2B, the integrated tubing and filter module (identified by the reference numeral 372) includes the filter 320 and all the tubing and related components described above which are connectable to apparatus 360. For example, the filter and tubing may be retained on a plastic support member 374 which is, in turn, connectable to apparatus 360 (e.g., connectable to the system housing 393 of the apparatus 360). When in the operative position connected to apparatus 360, flexible fluid conducting tubing lines to and from the filtration unit 320 are held in operative, pump communicative loops for operative contact with the peristaltic pumping members of the pumps 324, 344, 346 and 366 to cause the fluid to flow through the primary (blood) and secondary (processing fluid) circuits 312 and 340. Module 372, including filter 320 and all the tubing lines and associated flow components may be disposable after use. The peristaltic pumping members of pumps 324, 344, 346, and 366 may be fixedly disposed on apparatus 360 (without the disposable tubing loop components) and may be re-usable. In general, electrical, mechanical, or electromechanical components are also fixedly disposed in or on apparatus 360 (e.g., connectable to the system housing 393 of the apparatus 360). Examples of such components include the display screen 361, the bubble detector 326, line clamps 331 and connection apparatus for coupling to the transducer side portions of pressure pod apparatus used to implement pressure sensors 327, 328, 329 and 354 as will be described herein.

Measurements by the pressure sensors 327, 328, 329 and 354 may be used for one or more various control functions (e.g., used by the apparatus 360 in internal monitoring to make internal decisions and/or automatic adjustments to modify the fluid flow parameters). The present disclosure is not limited in the manner the pressure sensor measurements are used by the system in which they are present.

One or more of the pressure sensors 327, 328, 329 and 354 are provided with use of a pressure pod apparatus of a diaphragm type as described herein, for example, with reference to FIG. 1. One or more of the pressure sensors 327, 328, 329 and 354 used may be separated into two distinct portions because the tubing segments 314, 316 and 342, and all other flow components which come into contact with blood and/or blood waste products are preferably disposable. As such, at least the blood side components of these pressure sensors (e.g., the pressure pod apparatus 12 of each sensor as shown in FIG. 1) are thus also, at least in one embodiment, disposable (e.g., part of extracorporeal blood set 372). The electrical transducers are generally expensive and are thus it is desirable that they be incorporated into apparatus 360; and thus, are reusable.

For example, as shown in FIG. 1, a pressure sensor with disposable components may include a disposable portion such as the pressure pod apparatus 12 which includes the pressure pod body 11 (e.g., a rigid, plastic casing sometimes referred to as a "pod"). The pressure pod apparatus 12 includes the diaphragm 14 disposed therein separating the pod body 11 into two fluid-tight compartments or cavities 17 and 13. The inlet 15 and the outlet 16 open into cavity 17 to allow liquid to flow into and through the cavity 17 (also referred to herein as the liquid side cavity). The other cavity 13 on the opposing side of the diaphragm 14 has at least one access point (e.g., generally only one access point) to allow for fluid communication therewith (e.g., for communication of a dry gas such as air with the cavity 13 (although wet/wet transducers may also be usable with the pressure pod apparatus 12)). This cavity 13 is also referred to herein as the transducer side cavity or compartment because a transducer is in pressure-sensing communication with the air (e.g., a dry gas) on this transducer side of diaphragm 14. As used herein, air, gas, and dry gas are used interchangeably.

At least in one embodiment, the pressure pod apparatus 12 including the diaphragm 14 is the disposable part of the pressure sensor (e.g., pressure sensor 327, 328, 329 and 354). When the pressure pod apparatus 12 is used with apparatus 360, apparatus 360 may include a corresponding mating receptacle (e.g., as part of a connection apparatus) in and/or to which each disposable pod apparatus 12 is connected (e.g., the mating receptacle being shown generally by the connection apparatus 40 in FIG. 1 provided and/or mounted on system housing 27) putting the transducer side cavity 13 into fluid communication with, for example, a pressure sensing transducer disposed in the apparatus 360. Further, the transducer side cavity 13 may also simultaneously be put in fluid communication with an internal control unit/fluid tubing system (see, for example, FIG. 3).

Liquid flowing through the flow side cavity 17 of such a pressure pod apparatus 12 has an inherent fluid pressure which acts on the diaphragm 14 by moving it. When the diaphragm moves, the diaphragm either compresses or allows expansion of the fluid/dry gas in the transducer side cavity 13 (e.g., on the transducer side of the diaphragm 14). Compression of the fluid in the transducer side cavity 13 is generally shown using dashed line 19 in FIG. 1 and expansion of the fluid in the transducer side cavity 13 is generally shown using dashed line 18 in FIG. 1. The pressure of the compressed or expanded fluid is sensed by the corresponding pressure transducer inside the control apparatus 360. Such a transducer is schematically shown as pressure transducer 28 in FIG. 1. The pressure transducer 28 converts the sensed pressure to an electrical signal which is sent to a controller, such as controller 34 shown in FIG. 1 (e.g., an electrical microprocessing unit in control apparatus 360 for analysis of the signals or for interpretation of the signal as a pressure value), which may then process the signal for display, storage or use by software (or hardware) for calculations, or for carrying out any other functionality. The same or different controller or processing unit of apparatus 360 may be used for processing signals from position sensor 32 to provide control signals for repositioning the diaphragm 14 of the pressure pod apparatus 12 toward a centered measuring position (e.g., via control of an air pump of apparatus 360 corresponding to air pump 36 shown in FIG. 1).

The connection apparatus 40 as shown in FIG. 1, for example, provided as part of the system housing 27 or mounted thereon (e.g., a mating receptacle such as a receptacle mounted on the system housing 393 of the apparatus 360 as shown in FIGS. 2A-2B), may be of any suitable configuration for use in coupling with the pressure pod apparatus 12 and putting the transducer side cavity 13 into fluid communication with, for example, a pressure sensing transducer 28 (e.g., a pressure sensing transducer disposed in the apparatus 360 coupled by tubing to the connection apparatus 40). For example, such pressure pod apparatus 12 and mating connection apparatus 40 (e.g., receptacles) may include configurations like those shown in FIGS. 6-8. However, any suitable configuration of the pressure pod apparatus 12 and mating connection apparatus 40 may be used.

At least in one or more embodiments, the connection apparatus 40 includes retention structure for coupling to and retaining one or more portions of the pressure pod apparatus 12 therein (e.g., maintaining the pressure pod apparatus in a stable fixed position, but still being removable from the receptacle). Further, for example, such connection apparatus 40 may provide a port to connect the transducer side cavity 13 to the pressure transducer 28 contained in the system housing 27 when the pressure pod body 12 is mounted on the system housing 27 by the connection apparatus 40. Further, for example, the position sensor 32 may be provided as part of or positioned with the connection apparatus 40 as will be described herein.

In other words, the pressure pod apparatus 12 may be of one or more various configurations. For example, the pod body 11 may take any shape as long as a diaphragm 14 separates the liquid side cavity 17 from the transducer side cavity 13 and permits effective transfer of pressure from the a liquid flow in liquid side cavity 17 to transducer side cavity 13. For example, the body shape may be generally cylindrical and lie along axis 39 as shown in FIG. 1. In such a cylindrical configuration, the pod body portion 22 may include a generally concave surface 53 lying along axis 39 facing diaphragm 14 and spaced a distance therefrom. Further, the base body portion 24 may include a generally concave surface 55 lying along axis 39 facing diaphragm 14 and spaced a distance from the diaphragm 14.

For example, in one or more embodiments, the pressure pod body 11 may be formed of one or more components or portions thereof sealed together or may be a unitary structure. For example, the pod body portion 22 may be a separate body component having a surface sealed against a separate base body portion 24 and clamping the diaphragm 14 therebetween. Further, one or more pressure pod bodies may be incorporated into the same housing with each of such pressure pod bodies having either the same or different shape (e.g., the same internal shape with the same diaphragm).

Further, the pressure pod body 11 may be formed of any suitable material such as a polymer (e.g., polyvinyl chloride, polycarbonate, polysulfone, etc.). Further, the material may be optically transparent to enable a user to view the position of the diaphragm.

Figure 6A:
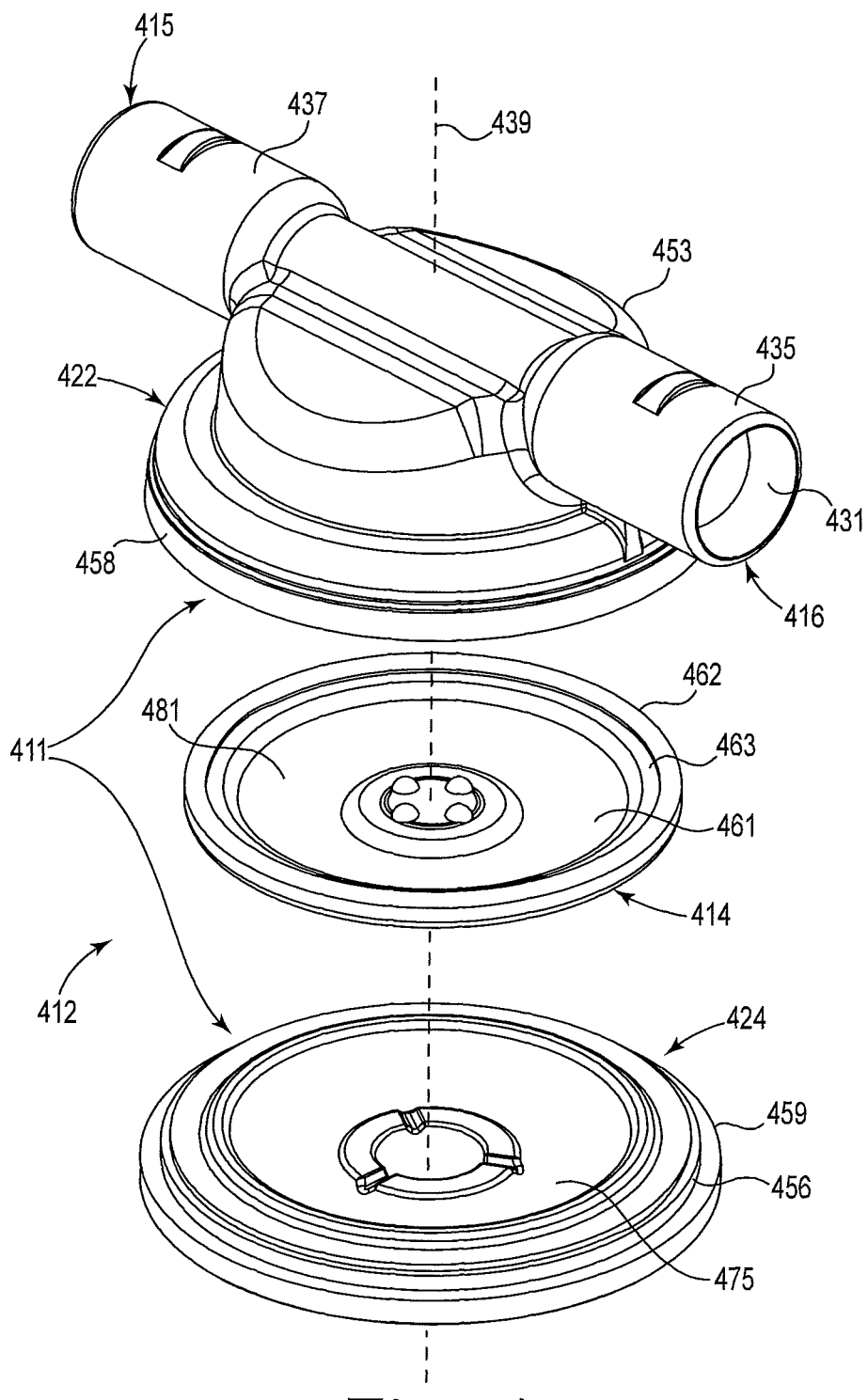
FIGS. 6A-6C show an exploded top perspective view, an exploded bottom perspective view, and an exploded side view of an exemplary pressure pod apparatus.
Figure 6B:
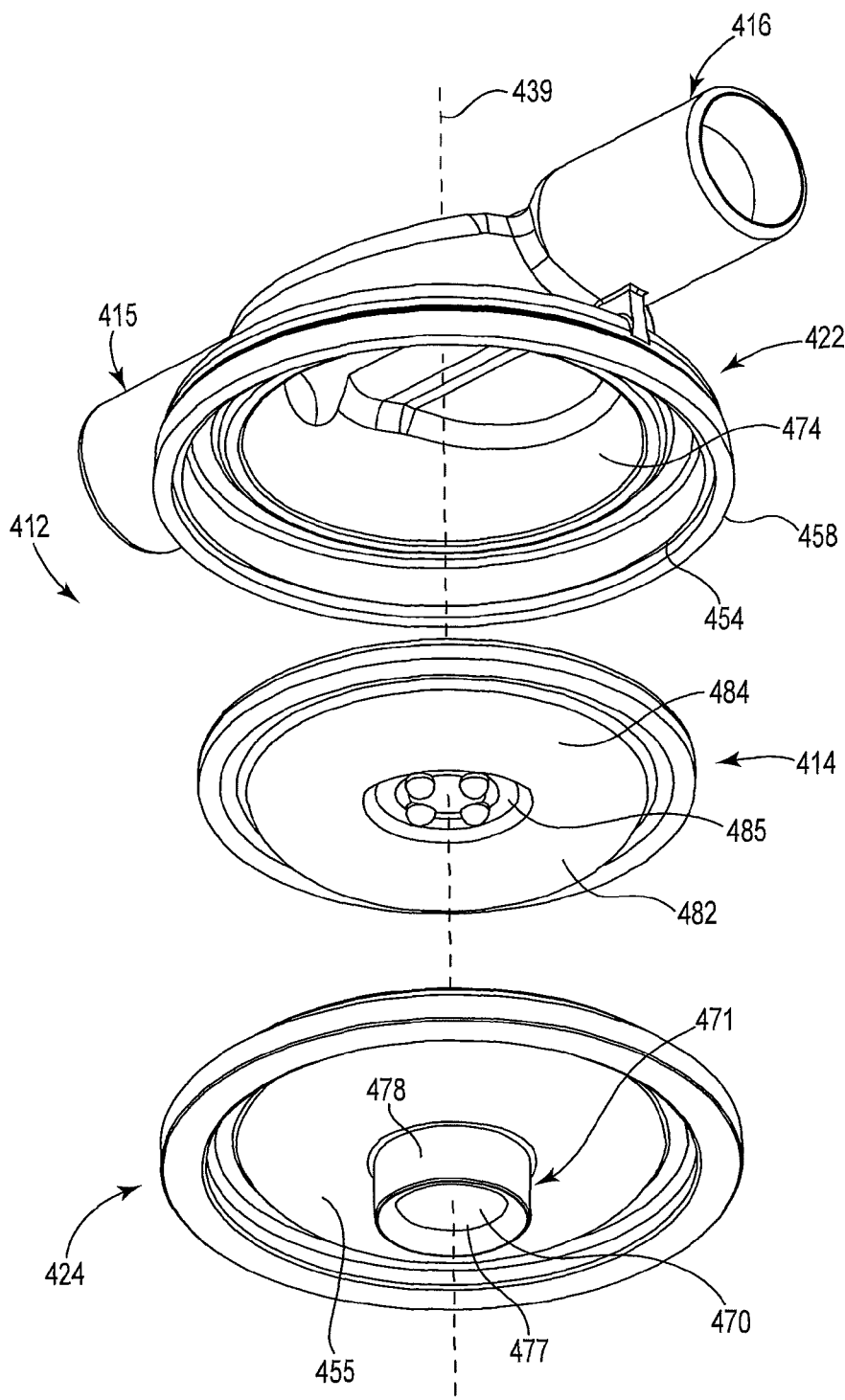
Figure 6C:
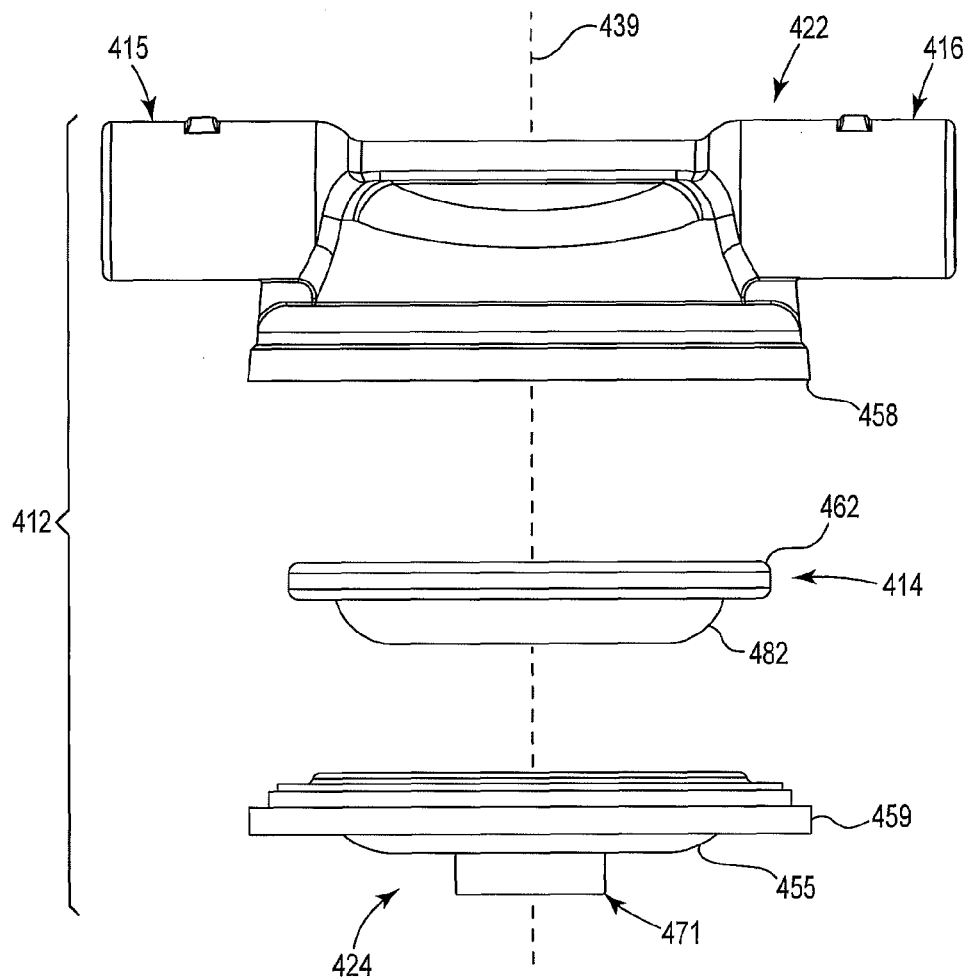

Figures FIG. 6A-6C show an exploded top perspective view, an exploded bottom perspective view, and an exploded side view of one embodiment of an exemplary pressure pod apparatus 412. The pressure pod apparatus 412 includes a pressure pod body 411 including at least a pod body portion 422 and a base body portion 424. For example, the pod body portion 422 which defines at least a portion of the liquid side cavity 417 (see, FIG. 8) may include an annular clamping portion 454 extending from an annular edge 458 inward towards axis 439. A generally concave portion 453 (e.g., which includes an inner surface 474 adjacent the liquid side cavity 417) is located inward of the annular clamping region 454 relative to axis 439. The generally concave portion 453 or dome section terminating the annular clamping region 454 along axis 439 (e.g., a generally concave portion facing the base body portion 424 and lying along the axis 439 with its center on the axis 439) includes an inlet 415 and an outlet 416 extending from the pod body portion 422 (e.g., from the generally concave portion 453) to allow, for example, connection of tubing thereto, and to provide a path for liquid to enter and exit the liquid side cavity 417. For example, each of the inlet 415 and outlet 416 includes a cylindrical element 435 defining an inner surface 431 for mating with a tube. The cylindrical element 435 also includes an outer surface 437 configured for mating with connection apparatus (e.g., such as to mate with retention structure of a receptacle such as that shown in FIGS. 7-8).

The base body portion 424, for example, which defines at least a portion of the transducer side cavity 413 (see, FIG. 8) may include an annular clamping portion 456 extending from an annular edge 459 inward towards axis 439. A generally concave portion 455 (e.g., which includes an inner surface 475 adjacent the transducer cavity 413) is located inward of the annular clamping region 456 relative to axis 439. The generally concave portion 455 or dome section terminating the annular clamping region 456 along axis 439 (e.g., a generally concave portion facing the pod body portion 422 and lying along the axis 439 with its center on the axis 439) includes a cylindrical port 471 including an access opening 470 (e.g., defined through the generally concave portion 455) to allow, for example, fluid communication between the transducer side cavity 413 and a pressure transducer provided as part of the fluid processing system (e.g., as part of the control apparatus 360 shown in FIGS. 2A-2B). For example, the port 471 may include an inner surface 477 which may receive a portion of a connection apparatus (e.g., such as to mate with a receptacle such as that shown in FIGS. 7-8). Further, for example, the port 471 may include an outer surface 478 which may mate with a portion of a connection apparatus (e.g., such as to mate with a receptacle such as that shown in FIGS. 7-8). Further, the mating between the port 471 and the connection apparatus may provide a seal therebetween (e.g., such that transducer side cavity 413 is a fluid tight cavity (e.g., when taking into consideration the other pressure sensing components such as tubing, pumps, etc.). Such a seal may be provided in any suitable manner, such as with use of a sealing device (e.g., an o-ring, sealing material, etc.).

The pressure pod apparatus 412 further includes diaphragm 414. For example, the diaphragm 414 includes an annular clamp region 463 extending from an annular edge 462 inward towards axis 439. A deflection portion 461 (e.g., which includes a first surface 482 adjacent the transducer side cavity 413 and a second surface 481 adjacent the liquid side cavity 417) is located inward of the annular clamp region 463 relative to axis 439. The deflection portion 461 may include a bias such that it includes one or more regions which extend further in the transducer side cavity 413 than other regions thereof, or a bias such that it includes one or more regions which extend further into the liquid side cavity 417 than other regions, which may be referred to as a diaphragm bulge (e.g., an annular region 484 of the deflection portion 461 extends into the transducer side cavity further than a center region 485 at axis 439 as shown in FIG. 6, or for other configurations this may be reversed as shown in FIG. 8). Depending on whether the pressure to be measured is positive or negative, the diaphragm bulge may be placed in a specific direction giving a larger range in the pressure range of interest (e.g., either positive or negative). The annular clamp region 463, when the pressure pod apparatus 412 is assembled, is clamped between annular clamping region 456 of the base body portion 424 and the annular clamping region 454 of the pod body portion 422 to form the cavities 413 and 417 on either sides of the diaphragm 414. Any suitable processes and materials may be used to provide such an assembly (e.g., adhesives, thermal processing, etc.).

Figure 7A:
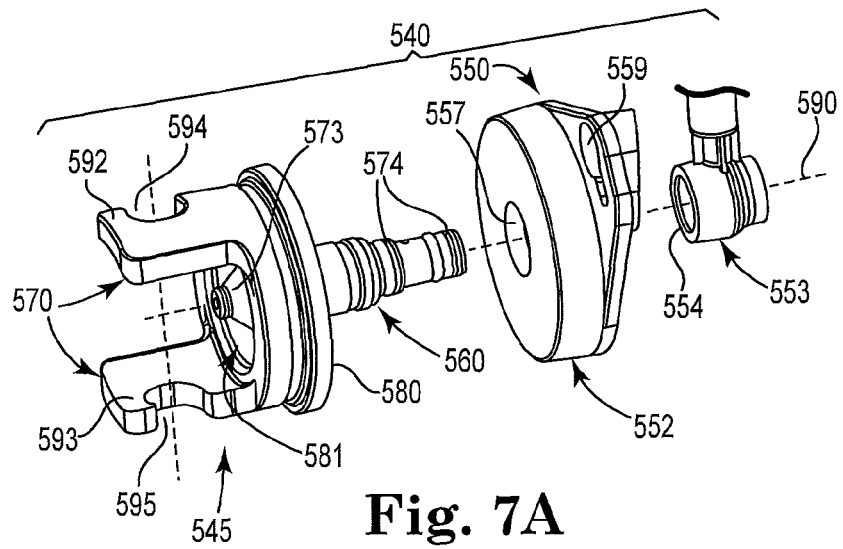
FIGS. 7A-7B show an exploded perspective view and a bottom view of a connection apparatus to connect a pressure pod apparatus, such as shown in FIGS. 6A-6C, to a fluid processing system (e.g., mount the pressure pod apparatus on a system housing).
Figure 7B:
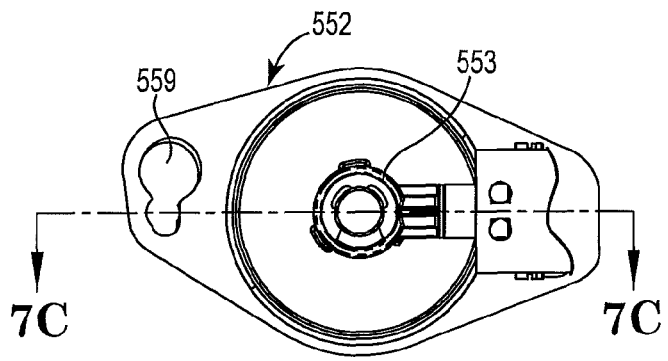
Figure 7C:
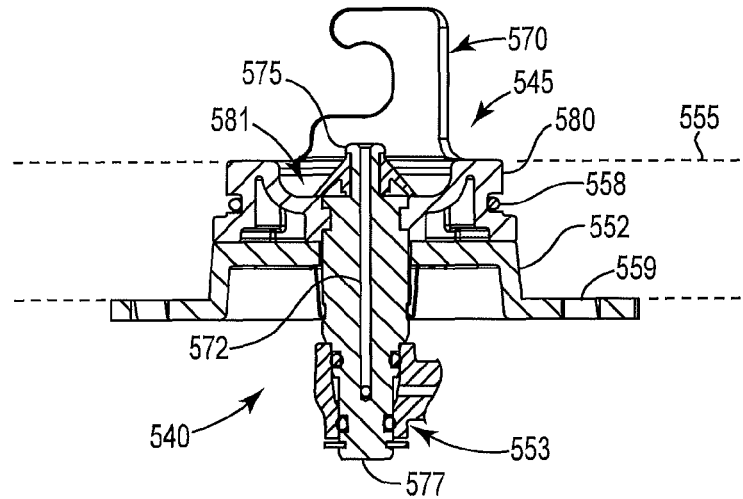
FIG. 7C is a cross-section of the connection apparatus shown in FIG. 7B taken at line C-C.

FIGS. 7A-7B show an exploded perspective view and a bottom view of a connection apparatus 540 mountable on a system housing (e.g., such as system housing 27 shown in FIG. 1 or system housing 393 of FIGS. 2A-2B) to connect a pressure pod apparatus (e.g., provided as part of a disposable extracorporeal blood set), such as pod apparatus 412 shown in FIGS. 6A-6C, to a fluid processing system (e.g., such as fluid processing system 360 shown in FIGS. 2A-2B). FIG. 7C is a cross-section of the connection apparatus 540 shown in FIG. 7B taken at line C-C.

For example, the connection apparatus 540 may include a receptacle 545 configured to mate with a pressure pod apparatus (e.g., retain pressure pod apparatus 412 therein in a particular fixed position), and mounting apparatus 550 for mounting the mating receptacle 545 with respect to a system housing (see dashed system housing 555 in FIG. 7C). For example, mounting apparatus 550 may include an internal mounting structure 552 for receiving at least a portion of the mating receptacle 545 (e.g., port 560) in an opening 557 defined therein aligned with an opening defined in system housing 555. Further, the mounting apparatus 550 may include an internal connection structure 553 (e.g., tubing and tubing connectors that mate with a portion of the mating receptacle 545 (e.g., port 560) when inserted through the opening 557 of the internal mounting structure 552 to allow for fluid communication from inside of the system housing 555 to the transducer side cavity 417 of the pressure pod apparatus 412. The mounting of the mating receptacle 545 to the housing may be implemented with use of at least one of the internal mounting structure 552 being mounted to the system housing 555 (e.g., via one or more fasteners using openings 559), the internal connection structure 553, interference fit between a part of the mating receptacle 545 with the internal mounting structure 552 (e.g., an interference fit between a portion of the port 560 within the opening 557 defined in the internal mounting structure 552), or in any other suitable manner to provide a fixed mating receptacle 540 on the system housing 555 and/or relative thereto. Further, for example, an o-ring 558 or other suitable sealing device may be used to prevent liquid ingress into the interior of the system housing 555.

The mating receptacle 545 may include an annular body portion 580 extending along axis 590 defining a receiving region 581 to receiving a portion of the pressure pod apparatus 412 (e.g., to receive at least a part of the pod body portion 424 thereof). The port 560 (e.g., an elongate structure providing a fluid channel 572 therethrough) may extend along axis 590 through the annular body portion 580 from a first end region 575 to a second end region 577. The first end region 575 is configured for coupling with the port 471 of the pressure pod apparatus 412 (e.g., mate with the inner surface 477 thereof). For example, the mating between the port 471 and the first end region 575 of the port 560 may provide a seal therebetween (e.g., such that transducer side cavity 413 is a fluid tight cavity (e.g., when taking into consideration the other pressure sensing components such as tubing, pumps, etc.). For example, one or more lip seals 573 may be provided at the first end region 575 to sealingly mate with the inner surface 477 of the port 471 of the pressure pod apparatus 412. However, such seal to provide a fluid tight connection may be provided in any suitable manner, such as with use of any sealing apparatus on any of the components (e.g., an o-ring, sealing material, etc.).

The second end region 577 is configured for coupling with the internal connection apparatus 553 (e.g., mate with an inner surface 554). For example, the mating between the internal connection apparatus 553 and the second end region 577 of the port 560 may provide a seal therebetween (e.g., such that transducer side of the pressure sensor components provide fluid tight communication between the transducer side cavity 413 of the pressure pod apparatus 412 and a pressure transducer contained with the system housing 555. For example, one or more o-ring seals 574 may be provided at the second end region 577 to sealingly mate with the inner surface 554 of the internal connection apparatus 553. However, such a seal to provide the fluid tight connection may be provided in any suitable manner, such as with use of any sealing apparatus on any of the components (e.g., an o-ring, sealing material, etc.).

The mating receptacle 545 also may include retention structure 570 for coupling to and retaining one or more portions of the pressure pod apparatus 412 therein (e.g., maintaining the pressure pod apparatus in a stable fixed position). For example, as shown in FIGS. 7A and 7C, the retaining structure 570 may include U-shaped elements 592 and 593 positioned relative to and/or extending from the annular body portion 580 at a distance from axis 590. Such U-shaped elements 592-593 define channel openings 594-595 that are open in opposing directions and which lie along an axis 591 (e.g., an axis 591 that is orthogonal to axis 590). The channel openings 594-595 are configured to receive a portion of each of the inlet 415 and outlet 416 (e.g., which also lie along an axis), respectively (e.g., receive the outer surface 437 of each cylindrical element 435 configured for mating within the respective channel openings 594-595 of retention structure 570 (e.g., upon aligning the axis 439 of the pressure pod apparatus 412 with the axis 590 of the receptacle 545 and pushing and/or turning the pressure pod apparatus 412 about the axis 590 such that the outer surface 437 of each cylindrical element 435 is mated within the respective channel openings 594-595 of retention structure 570). However, any suitable mating configurations that provide for stable positioning of the pressure pod apparatus 412 on the system housing may be used and the present disclosure is not limited by only the mating configurations described herein.

Figure 8A:
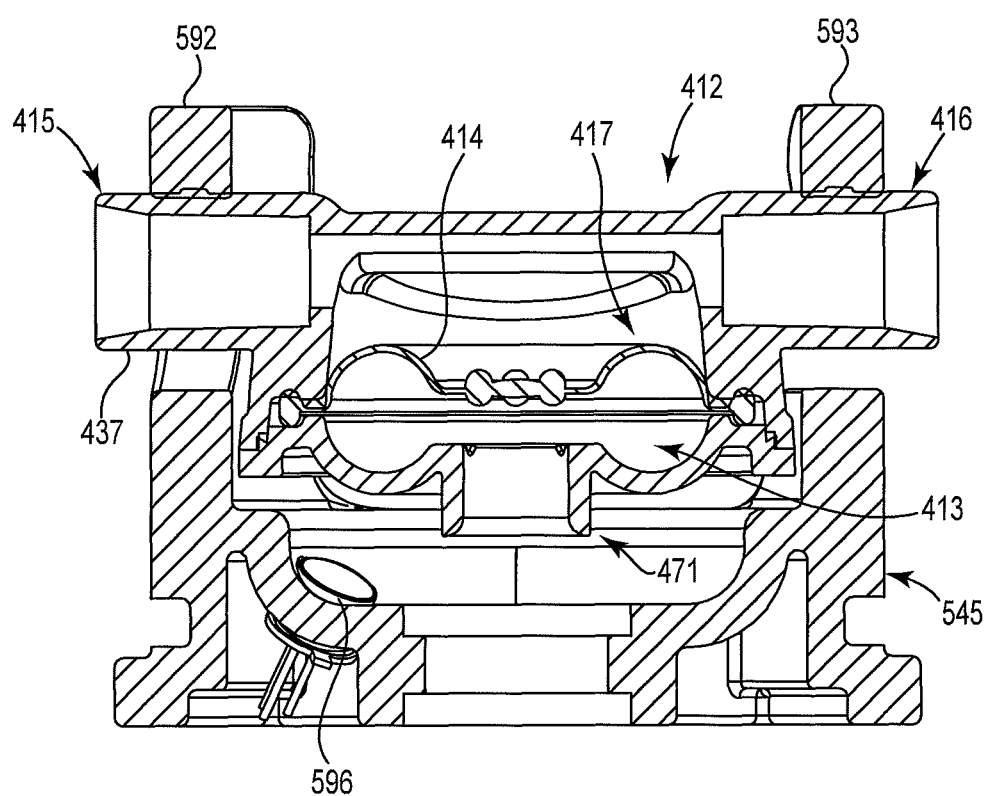
FIGS. 8A-8B show a first side cross-section view and a second side perspective cross-section view (orthogonal of the first side cross-section view) of a pressure pod apparatus (such as shown in FIGS. 6A-6C) mounted in a connection apparatus (such as shown in FIGS. 7A-7C) and including components for use in sensing position.
Figure 8B:
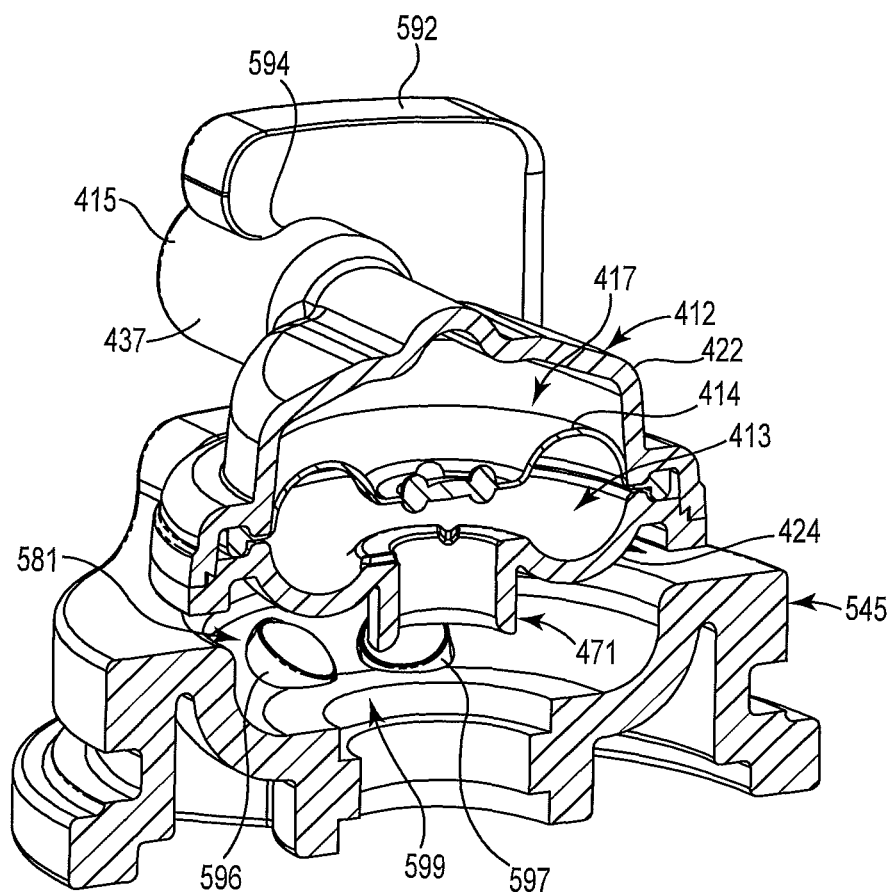
Figure 8C:
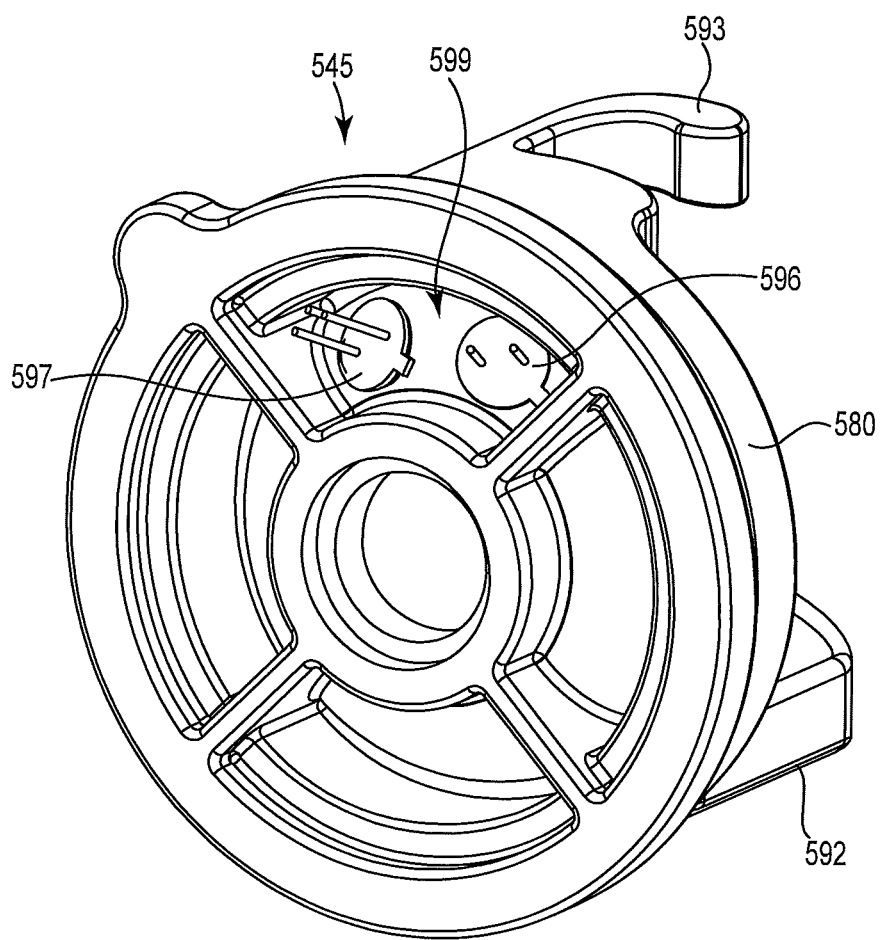
FIG. 8C shows a bottom perspective view of a portion of the connection apparatus shown in FIGS. 8A-8B and including components for use in sensing position.

FIGS. 8A-8B show a first side cross-section view and a second perspective cross-section view (orthogonal to the first side cross-section view) of, for example, pressure pod apparatus 412 (such as shown in FIGS. 6A-6C) mounted in, for example, connection apparatus 540 (e.g., mounted in receptacle 545 such as shown in FIGS. 7A-7C). Further, components for use in sensing position are also shown as described herein. FIG. 8C shows a bottom perspective view of a portion of the connection apparatus 540 shown in FIGS. 8A-8B.

In other words, for example, as shown in FIGS. 8A-8C, the outer surfaces 437 of each cylindrical element 435 of the inlet and outlets 415, 416 of pressure pod apparatus 412 is shown as being received within the respective channel openings 594-595 of retention structure 570 such that the pressure pod apparatus 412 is fixedly positioned within the receptacle 545 and relative to system housing 555. The cross-section views thereof show the diaphragm 414 separating the liquid side cavity 417 defined at least in part by the pod body portion 422 from the transducer side cavity 413 defined at least in part by the base body portion 424. Some components of the connection apparatus 540 have been removed from the FIGS. 8A-8C to more easily show other components (e.g., the port 560 is not shown such that the optical transmitter/receiver devices present in one or more embodiments of systems described herein can more easily be seen).

Figure 3:
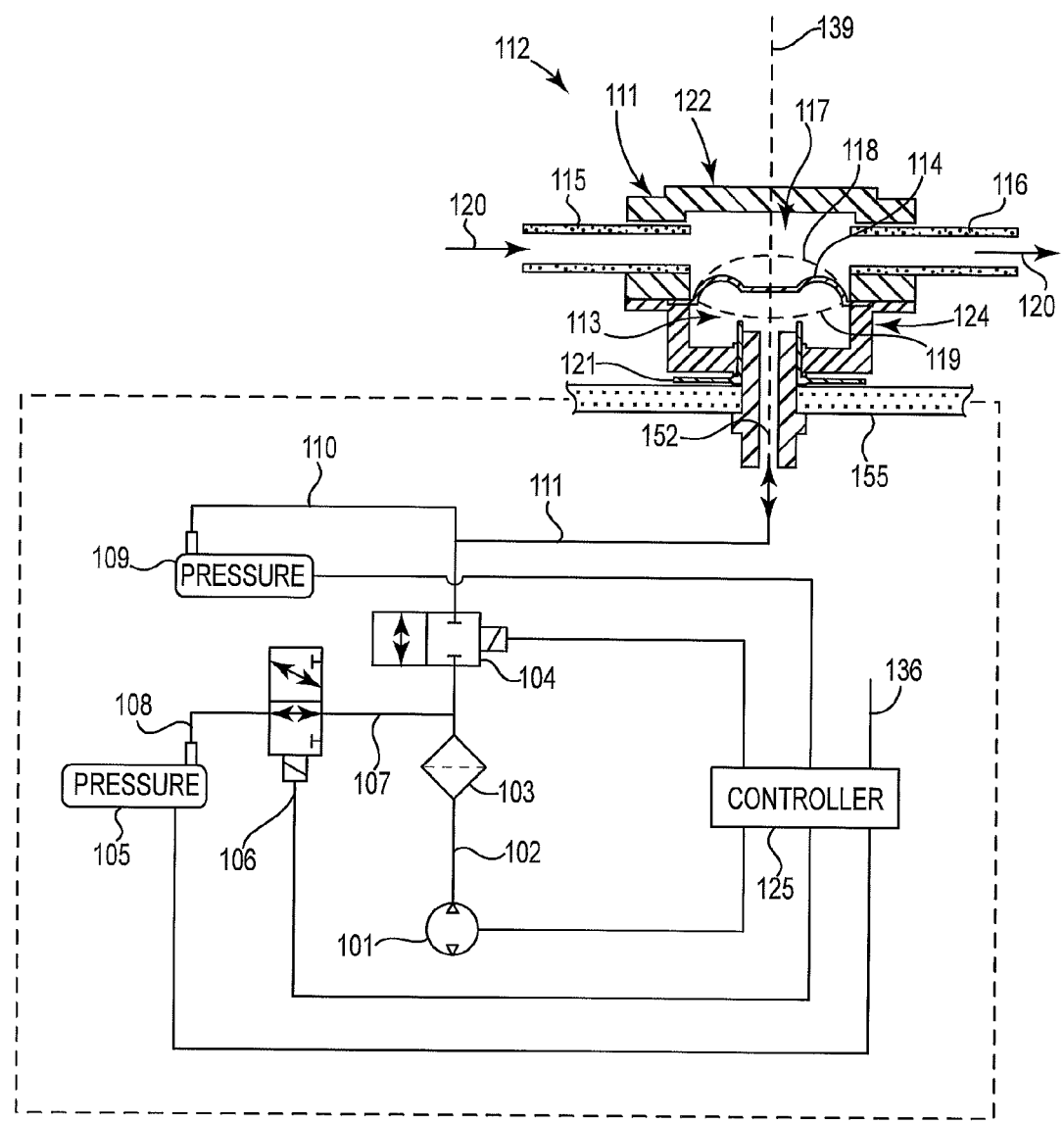
FIG. 3 is an illustrative diagram showing a portion of a fluid processing system including a pressure pod apparatus connected to components within a system housing containing, for example, a controller and pressure transducer.

FIG. 3 is an illustrative diagram showing a portion of an extracorporeal fluid system (e.g., such as may be used in a system shown and described with reference to FIGS. 2A-2B) including connection of a removable pressure pod apparatus 112 (such as pressure pod apparatus 412 shown in FIGS. 6 and 8) to a system housing 155 (e.g., a system housing that contains one or more pressure transducers, a controller, valves, tubing, etc., such as housing 393 of FIGS. 2A-2B). Connection apparatus (or point of connection) between the pressure pod apparatus 112 and the system housing 155 (including to the components therein) is shown generally as apparatus 121 (e.g., such connection apparatus 121 may be similar to that used to mount pressure pod apparatus 412 in mating receptacle 545 of connection apparatus 540 shown in FIGS. 6-8, and such as may be associated with apparatus 360 shown and described with reference to FIGS. 2A-2B).

In one or more embodiments, the pressure pod apparatus 112 may include a pressure pod body 111 that includes at least a pod body portion 122 and a base body portion 124 (e.g., a pressure pod body that may be coupled in a mating receptacle). As shown in the exemplary embodiment of FIG. 3, a diaphragm 114 (e.g., a flexible membrane) separates the liquid side cavity 117 defined at least in part by the pod body portion 122 from the transducer side cavity 113 defined at least in part by the base body portion 24. The transducer side cavity 117 is in fluid communication with an inlet 115 and an outlet 116 (e.g., through which liquid flows as indicated by arrows 120). The diaphragm 114 is displaceable from a centered measuring position (e.g., along axis 139) into the liquid side cavity 117 towards the pod body portion 122 as shown by dashed line 118 and is displaceable from the centered measuring position (e.g., along axis 139) into the transducer side cavity 113 towards the base body portion 124 as shown by dashed line 119. In other words, the flexible diaphragm 114 may flex as generally shown by positions 119 and 118.

As shown in the exemplary embodiment of FIG. 3, when in use, liquid would flow within the extracorporeal circuit between the inlet 115 and the outlet 116 of the pressure pod apparatus 112. The pressure of the liquid in liquid side cavity 117 flexes the diaphragm 114 until the pressure or force on both sides of the diaphragm 114 equalize. The flexible diaphragm 114 expands and contracts based upon the pressure exerted in the liquid side cavity 117 and the mass of gas in the connected tubing and transducer side cavity 113 (e.g., air cavity), atmospheric pressure, and temperature. For example, as shown in the exemplary embodiment of FIG. 3, to measure the pressure exerted by the fluid (e.g., liquid such as blood) in liquid side cavity 117, a pressure transducer 109 is connected through a series of tubes 110 and 111 to the transducer side cavity 113 (e.g., via a port defining a channel 152 extending through the connection apparatus 121) while a valve 104 (e.g., a 2 port/2 way solenoid valve) is closed. For example, such connection tubes used for connecting the pressure transducer 109 to the transducer side cavity 113, or other connection tubing described or used herein, may be made from a polymer material suitable for preventing leakage in the pressure range of −700 to 700 mmHg.

In addition to sensing the pressure in liquid side cavity 117, the exemplary system shown in FIG. 3 also provides for automatically (e.g., without user manual intervention such as a check and/or reposition process described in the Background section herein) repositioning the diaphragm 114 towards the centered measuring position. For example, as further described herein, such repositioning may be implemented by sensing the position of the diaphragm 114, generating a control signal based on the sensed position of the diaphragm 114, and repositioning the diaphragm 114 towards the centered measuring position (e.g., the position used to take pressure measurements using pressure transducer 109) based on the control signal. To position the diaphragm 114 centrally, air may be infused or extracted using a pump configuration (e.g., an air pump 101 connected to the transducer side cavity 113 through the 2 port/2 way solenoid valve 104).

For example, during the powered off state of the solenoid valve 104, the total volume of air ($V_1$) associated with the pressure sensing (e.g., in the pressure sensor circuit), such as in the pressure transducer 109, tubing 110, 111, air channel 152, and cavity 113 of the pressure pod apparatus 112, is sealed and leak free. In other words, in this embodiment, the total volume $V_1$ is the volume of air enclosed within the space encompassed within the tubing 110, 111, pressure transducer 109, channel 152, and transducer side cavity 113 associated with the pressure pod apparatus 112. As the pressure in the liquid side cavity 117 increases and decreases the volume of air will compress and expand according to the ideal gas law and due to the elasticity of the enclosed space.

The ideal gas law is the equation of the state of an ideal gas. It is a good approximation to the behavior of the gas under the temperature and pressure conditions to which the pressure pod apparatus and system may be exposed. The state of an amount of gas is determined by its pressure, volume, and temperature. The modern form of the equation is:

$$pV=nRT$$

where p is the absolute pressure of the gas; V is the volume; n is the amount of substance; R is the gas constant; and T is the absolute temperature. The compliance of the enclosed chamber may be calculated as follows:

$$C=Vc/Pa$$

where C is the compliance of the enclosed chamber, Vc is the volume of the enclosed chamber and Pa is the atmospheric pressure.

The volume of gas within the enclosed sealed space ($V_1$) associated with the pressure sensor components (e.g., in the pressure sensor circuit) may be increased or decreased by adding or subtracting additional gas molecules using the air pump 101. For example, air may be infused into the air cavity 113 of the pressure pod apparatus 112 using the air pump 101 by opening the valve 104. Opening of the valve 104 connects the pump cavity volume ($V_2$) to the volume $V_1$. For example, this volume $V_2$ may be the air volume encompassed within the tubing 102, 107, air filter 103, and air pump 101. To avoid a build up of dust over time, a particle filter 103 may be placed at the outlet of the pump 101 and connected to the air pump 101 using tubing 102.

If too much air is infused into the transducer side cavity 113 of the pressure pod apparatus 112, the diaphragm 114 will distend toward the liquid side cavity 117 (e.g., blood side) and if too little air is present it will distend towards the air side cavity 113 of the pressure pod apparatus 112. Since the diaphragm 114 is flexible, its effective compliance will be larger and the change in pressure for a given volume infusion of air will be zero as long as the diaphragm 114 exerts no tension. Once the diaphragm comes into tension or touches the sides of the pod body 111, the compliance will dramatically reduce, and as air is infused, the slope of the pressure rise will dramatically increase.

As such, in the embodiment of FIG. 3, before the solenoid valve 104 may be opened, the pump pressure (in the pump air circuit as measured by pressure transducer 105) should equal the pressure measured by the pressure transducer 109. Otherwise, a volume of air may be infused or extracted from volume $V_1$ resulting in a repositioning of the diaphragm 114. This is avoided by controlling the pump pressure using the pressure transducer 105 as feedback to equate to the pressure measured by the pressure transducer 109 before the valve 104 is opened. For example, when the solenoid valve 106 is powered off, the pressure transducer 105 is connected to the air pump 101, and when the solenoid valve 106 is powered on, the pressure transducer 105 is connected to atmospheric pressure.

In other words, the pressure within the air pump circuit (e.g., including air pump 101) may be separately measured using the pressure transducer 105. It may be periodically auto-zeroed using the valve 106 (e.g., a 3 port/2 way solenoid valve). Auto-zeroing the air pump circuit may include venting the pressure transducer 105 to atmosphere to reduce and/or eliminate pressure offsets by measuring atmospheric pressure directly. When a gauge pressure sensor is connected to atmosphere and its reference is connected to atmosphere, the pressure read should be 0. Pressure transducers tend to be much more sensitive to drift in offset rather than gain and using the strategy of reading the pressure transducer offset and subtracting it from all subsequent readings enables the elimination of any offset drift as a device warms up. It also allows the elimination of any pressure offset of pressure transducer 109 by the comparison with pressure transducer 105 without the requirement for separate auto-zeroing of the pressure transducer 105. When both transducers are connected together, any difference may be assumed to be as a result of an offset drift. With such a strategy, if multiple pressure transducers are employed, a single air pump circuit may be connected to multiple pressure pod apparatus ensuring a common pressure reference using pressure transducer 105.

In other words, at least in one embodiment, a first step to centering the diaphragm 114 towards a centered measuring position is to ensure the pressure in the pump air circuit (e.g., described herein as including pump 101), as measured by the pressure transducer 105 is at the same pressure measured by the pressure transducer 109 to prevent a large scale deflection of the diaphragm 114 when the valve 104 is powered open. Such deflection may occur if the air pump circuit pressure as measured by pressure transducer 105 was significantly higher or lower than the pressure measured by pressure transducer 109 (that of the air cavity 113 of the pod apparatus 112).

As set forth herein with reference to FIG. 1, various position sensors may be used to sense the position of the diaphragm 114 for use in repositioning the diaphragm 114 to the center position. For example, although not shown in FIG. 3, such position sensors may include a proximity sensor such as an electro-optical or capacitive proximity sensor to sense the position of the diaphragm 114. Various embodiments will be described with reference to FIGS. 6-12 which provide for the positioning and use of such a variety of position sensors. However, it will be recognized that various other types of position sensors may be used for sensing the position of diaphragm 114 or any of the diaphragms described herein in any other embodiments, and the present disclosure is not limited to the position sensors described herein, or the position sensor configurations or locations described herein. However, some may be beneficial over others.

As shown in the embodiment of FIG. 3, a controller 125 (e.g., within the system housing 155) is operatively coupled to receive one or more signals representative of the position of the diaphragm 114 (shown generally as position sensor input 136 to controller 125) from a position sensor (e.g., position sensor 122 shown in FIG. 4 as part of the embodiment of FIG. 3) to generate a control signal based thereon for use in repositioning the diaphragm 114 towards the centered measuring position. The air pump circuit of FIG. 3 may then be used to reposition the diaphragm 114 towards the centered measuring position based on the control signal generated by the controller 125.

Figure 4:
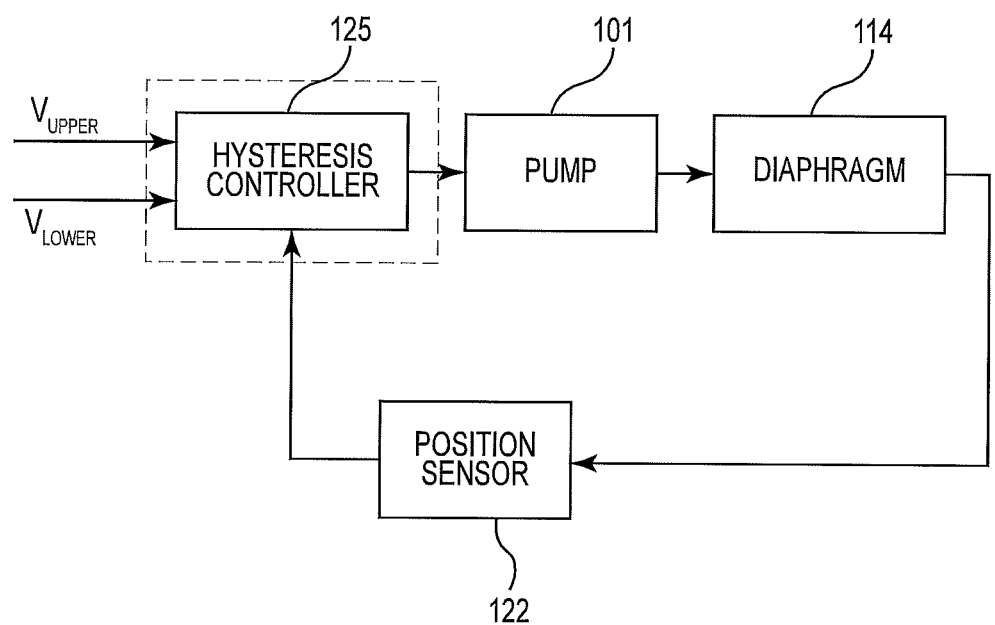
FIG. 4 is a control block diagram illustrating an exemplary control algorithm for repositioning a diaphragm of a pressure pod apparatus such as that shown generally in FIGS. 1 and 3.
Figure 5:
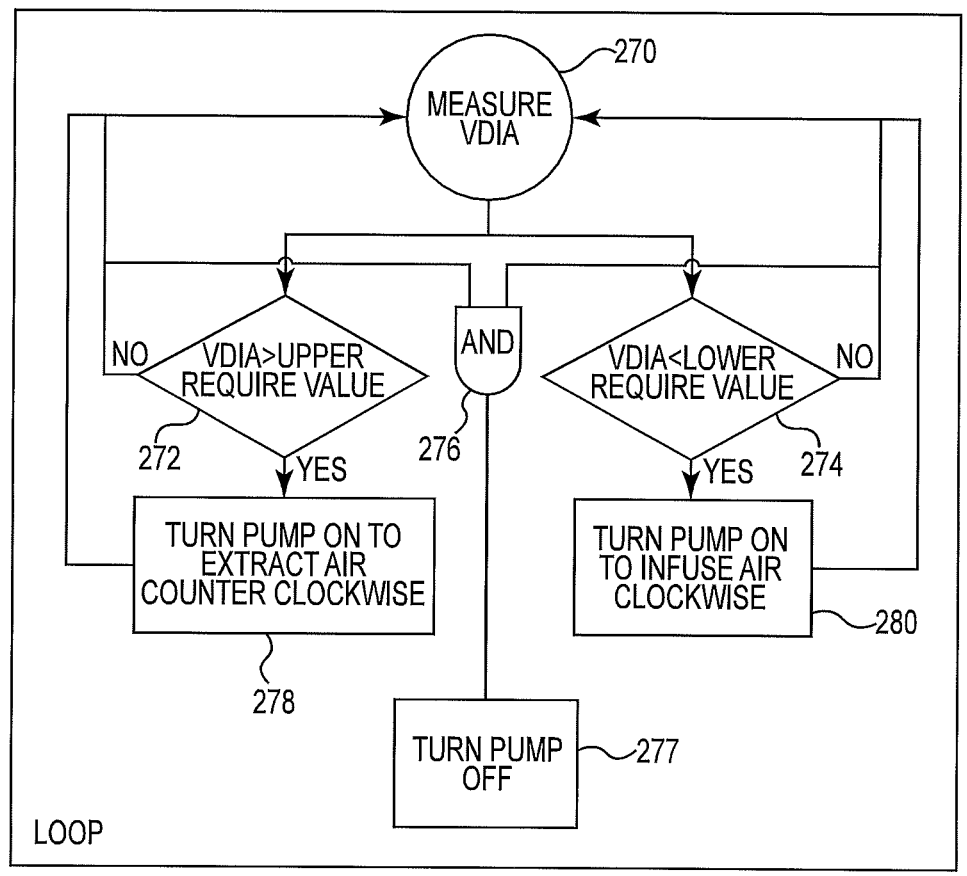
FIG. 5 is a flow diagram illustrating an exemplary control algorithm for repositioning a diaphragm of a pressure pod apparatus such as that shown generally in FIGS. 1 and 3.

For example, FIG. 4 shows a control block diagram illustrating an exemplary controller 125 in a control loop (e.g., feedback loop) capable of repositioning the diaphragm 114 of a pressure pod apparatus 112. FIG. 5 is a flow diagram illustrating an exemplary control algorithm which may be implemented by the controller 125 for repositioning the diaphragm 114 of the pressure pod apparatus 112.

As shown in FIG. 4, a predetermined range of acceptable diaphragm positions relative to the center position are set (e.g., which may be referred to as the centered measuring position). For example, Vupper and Vlower may correspond to acceptable centered measuring positions of diaphragm 114 to which the diaphragm 114 may be set for purposes of taking pressure measurement (e.g., using pressure transducer 109).

The controller 125, e.g., a hysteresis controller, may compare the sensed position of the diaphragm 114 (e.g., available using the position sensor 122) to the predetermined range and generate a control signal to control air pump 101 based on the comparison. For example, the sensed position of the diaphragm 114 may be provided by sensing the position of the diaphragm 114 at multiple times over multiple rotations of a pump (see apparatus 360 of FIGS. 2A-2B) providing for flow of the liquid through the liquid side cavity 117 from inlet 115 to outlet 116 and averaging the sensed position of the diaphragm 114 at the multiple times. In other words, in one or more embodiments, such diaphragm repositioning may be carried out whenever the position sensor senses a diaphragm position change outside a measurement position limit (e.g., Vupper or Vlower). In such a case, repositioning may occur immediately upon such detection. However, any manner of sensing position and/or processing of such position measurements may be used to provide a diaphragm position measurement for comparison to the range. For example, the diaphragm repositioning may be carried out on an hourly basis, or at any other desired interval.

As shown in FIG. 5, in one embodiment, the controller 125 may carry out the comparison shown therein for generating the control signal to control pump 101. In this exemplary embodiment, the air pump apparatus may include a peristaltic pump which may be driven clockwise to infuse air into the air or transducer side cavity or may be driven counter-clockwise to remove air from the air or transducer side cavity. For example, the diaphragm position measurement (Vdia) 270 may be compared to Vupper and Vlower (decision blocks 272 and 274). If Vdia is greater than Vupper then a control signal to turn on pump 101 and drive the pump 101 counter-clockwise is generated (block 278) to extract air from the transducer side cavity 113. The comparison process is then repeated. If Vdia is less than Vlower then a control signal to turn on pump 101 and drive pump 101 clockwise is generated (block 280) to infuse or add air to the transducer side cavity 113. The comparison process is then repeated. Further, if Vdia is less than Vupper and greater than Vlower (block 276) then a control signal to keep pump 101 off is generated (block 277). The comparison process is then repeated. Each of such control signals may be generated to reposition the diaphragm 114 towards a centered measuring position (e.g., within the range of acceptable positions). This process, in one embodiment, is run at a rate less than the leak rate of the system or pressure change which will cause the diaphragm to move outside its expected position limits. For example, and for simplicity, the rate at which the position is measured may be set in a range of 1 to 10 Hz and adequately filtered with a low pass filter to eliminate the effects of noise (e.g., a low pass filter having a cut off frequency of 0.1 Hz).

For example, in one embodiment, a specific voltage target range may be provided in a memory (e.g., nonvolatile random Access Memory (NVRAM)) associated and accessible with circuitry of controller 125. The voltage target range may be used for comparison to the sensed position (e.g., a voltage signal) and a control signal may be generated to control the air pump 101 to reposition the diaphragm 101 to ensure it is within the specific target range (e.g., is centered). For example, the voltage output target range for a correctly positioned diaphragm 114 may be set via calibration performed at the time of manufacturing. Such target range limits may also be reset in the field (e.g., such as by entering a service menu and setting limits based upon the maximum allowable diaphragm deflections). For example, the range may be set as a percentage of maximum deflections (e.g., bottomed out or topped out) or after its initial positioning based upon the examination of the rates of pressure change.

Further, for example, the liquid flow through the liquid side cavity 117 of the pressure pod apparatus 112 may be generated by a peristaltic pump. Such a peristaltic pump generates pulsatile flow which generates a pulsatile pressure signal resulting in a pulsatile deflection of the diaphragm 114. To determine the average position of the diaphragm 114 during such pulsatile flow it may be beneficial to filter the sensed diaphragm position (e.g., voltage representative of position). For example, the position of the diaphragm 114 may be measured every 20 msecs and averaged over five (5) rotations of a peristaltic pump using a filter (e.g., a boxcar filter). This average diaphragm position may then be fed to hysteresis controller 125 which determines if the value is inside or outside the predetermine position range (see, for example, FIG. 5). If the value is inside the position range, the hysteresis controller 125 does nothing, but if the value is outside the position range, the hysteresis controller 125 determines whether gas (e.g., air) is to be infused or drained from the circuit including the transducer side cavity 113.

Position sensing of the diaphragm 114 using a position sensor 122 may be implemented in a variety of ways using one or more different position sensing configurations. For example, FIGS. 8A-8C shall be used to describe implementation using one or more electro-optical position sensors. FIGS. 9-12 shall be used to describe implementation using one or more electrodes as part of a capacitive proximity or position sensor.

For example, as shown in FIGS. 8A-8C, in one or more embodiments an electro-optical sensor 599 is provided as part of the mating receptacle 545 of connection apparatus 540. For example, the electro-optical sensor 599 may include one or more optical transmitter devices 596 (e.g., light emitting diodes emitting electromagnetic radiation at any suitable wavelength, including infrared light (IR)) mounted in the defined receiving region 581 of the receptacle 545 to emit light in the direction of at least the diaphragm 414. Likewise, for example, the electro-optical sensor 599 may include one or more optical detection devices 596 (e.g., light detecting diodes suitable for detecting reflected electromagnetic radiation at any suitable wavelength corresponding to the light emitting devices, including infrared light (IR)) mounted in the defined receiving region 581 of the receptacle 545 to detect light reflected from the diaphragm 414. In one or more embodiments, the diaphragm material may be coated with an IR reflective material or may be formed of an IR reflective material (e.g., IR reflective materials such as titanium dioxide, silver, gold, aluminum, etc.). For example, the use of such reflective materials may eliminate potential effects which the liquid medium flowing in the fluid path of the liquid side cavity may have on the position measurement.

For example, the measuring arrangement may have at least one light transmitter (e.g., light emitting diode 596) to direct at least one light beam on a portion of the diaphragm 414 under control of controller 125 and at least one light detector (e.g., light detecting diode 597) to detect reflection of the light beam from the diaphragm 414 indicative of the position of the diaphragm 414. Under control of controller 125, the signal from the light detector is sampled as desired for use in providing a measurement signal representative of the position of the diaphragm 414. The measurement signal is then used, for example, as described with reference to FIGS. 4 and 5. Electrical connectors may be used to connect the leads (shown in FIG. 8C) of the optical devices to other devices (e.g., controller) within the system housing 155.

In one or more embodiments, synchronous demodulation may be used to eliminate the effects of ambient noise (e.g., such methodology is described in U.S. Pat. No. 6,947,131). For example, synchronous demodulation amplifies only the difference between the light emitting diode (LED) being turned on and it being turned off this removing the effects of ambient light which are present for both measurements.

It will be recognized that such optical sensor components may be positioned in any location suitable to provide for reflection and detection of light from the diaphragm 414 (e.g., with or on the receptacle, or with or on any other components of the system, such as the system housing). Further, in one or more embodiments, transmission of light through the diaphragm may be used for detecting position.

One will recognize that the electro-optical sensor may be provided in any suitable manner. The various locations and types of components described herein is not to be taken as limiting to the scope of the configurations of such sensors capable of providing a diaphragm position signal for use in repositioning the diaphragm to a centered measuring position.

Figure 9:
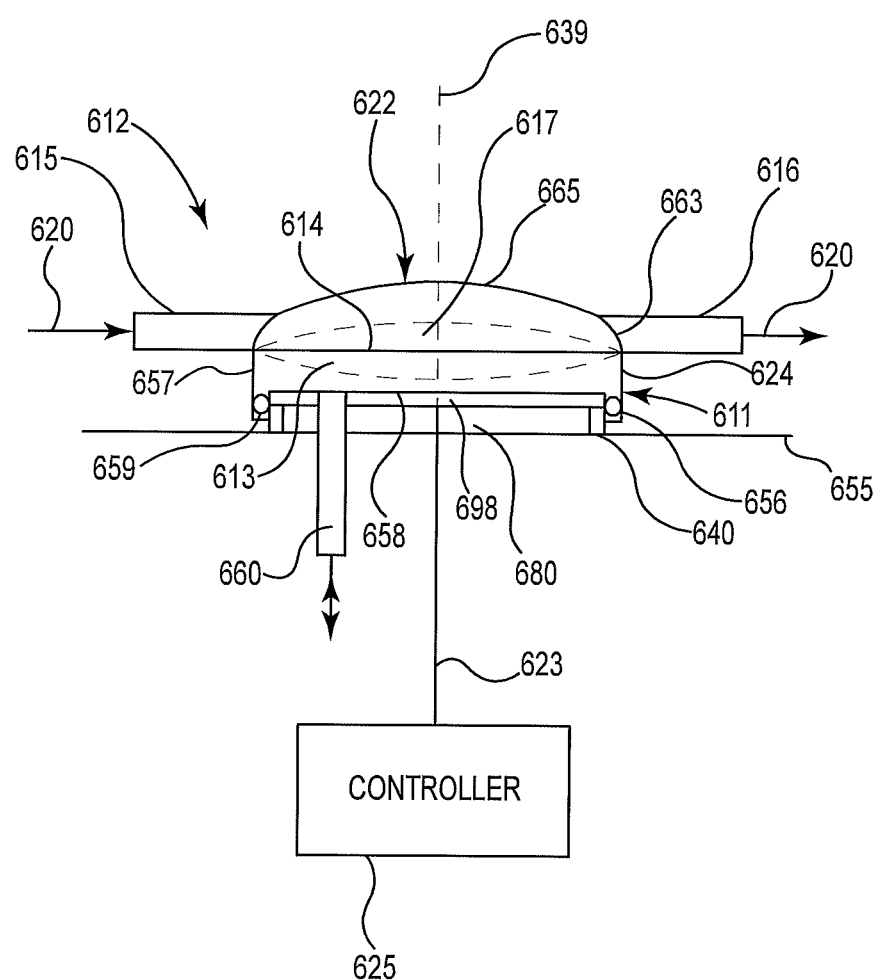
FIG. 9 is an illustrative diagram showing another exemplary pressure pod apparatus connected to components within a system housing containing for example, a controller and pressure transducer using a connection apparatus that includes components for use in sensing position.

Further, for example, as shown in FIGS. 9-12, a capacitive proximity sensor may be provided in one or more different manners to sense the position of a diaphragm in a pressure pod apparatus. For example, the use of a capacitive proximity sensor is generally shown with reference to FIG. 9. As shown in FIG. 9, an illustrative diagram showing a portion of an extracorporeal fluid system (e.g., such as may be used in a system shown and described with reference to FIGS. 2A-2B) includes connection of a pressure pod apparatus 612 to a pressure pod mating receptacle 640 (e.g., a mating receptacle such as one associated with an apparatus 360 shown and described with reference to FIGS. 2A-2B). The pressure pod apparatus 612 includes a pressure pod body 611 including at least a pod body portion 622 and a base body portion 624 (e.g., a base body portion that is coupled to a pressure pod mating receptacle 640).

For example, in one embodiment as shown in FIG. 9, the base body portion 624 which defines at least a portion of the transducer side cavity 613 may include a cylindrical section 657 lying along axis 639 terminating in a base section 658. An annular flange 656 may extend from the cylindrical section 657 past the base section 658 at the outer region thereof at a distance from the axis 639. The annular flange 656 may include a sealing device (e.g., an o-ring, sealing material, etc.) seated on or in an inner surface 659 of the annular flange 656 so as to engage and sealingly couple the base body portion 624 to the mating receptacle 640 (e.g., a cylindrical body sized to mate with the base body portion 624) and to provide an opening through which one or more components may pass, such as wires for attachment to a proximity sensor, a port 660 and/or tubing for access to the transducer side cavity, etc.

Further, for example, in one embodiment as shown in FIG. 9, the pod body portion 622 which defines at least a portion of the liquid side cavity 617 may include a generally cylindrical section 663 lying along axis 639 terminating in a dome section 665 (e.g., a generally concave portion facing the base body portion and lying along the axis 639 with its center on the axis 639). An inlet 615 and an outlet 616 extend from the pod body portion 622 to allow, for example, connection of tubing thereto, and to provide a path for liquid to enter and exit the liquid side cavity 617.

As shown in the exemplary embodiment of FIG. 9, diaphragm 614 (e.g., a flexible membrane) separates the liquid side cavity 617 defined at least in part by the pod body portion 622 from the transducer side cavity 613 defined at least in part by the base body portion 624. The transducer side cavity 617 is in fluid communication with the inlet 615 and an outlet 616 (e.g., through which fluid flows as indicated by arrows 620). The diaphragm 614 is displaceable from a centered measuring position (e.g., along axis 639) in the same manner as described with respect to other embodiments herein. Further, pressure measurements are obtained in a manner similar to other embodiments described herein (e.g., see the description with reference to FIG. 3).

In addition to sensing the pressure in liquid side cavity 617, the exemplary system shown in FIG. 9 also provides for automatically (e.g., without user manual intervention such as a check and/or reposition process described in the Background section herein) repositioning the diaphragm 614 towards the centered measuring position using a capacitive proximity sensor. For example, as shown therein, one or more electrodes 680 are positioned near the target or object (i.e., the diaphragm 614) to be sensed. In other words, each of the one or more electrodes 680 and the diaphragm 614 form a "capacitor." Such a capacitor generally has a capacitance that is given by the equation:

$$C = \frac{\varepsilon_0 K A}{d}$$

where C is the capacitance, $\varepsilon_0$ is the permittivity of free space constant, K is the dielectric constant of the material in the gap, A is the area of the plates, and d is the distance between the plates. Since the area of the electrode(s) 680 and the diaphragm 614 generally remain constant, and the dielectric of the material in the gap (e.g., air) also remains constant, any change in capacitance is a result of a change in the distance between the electrode(s) 680 and the diaphragm 614. In other words, the capacitive equation above can be simplified to:

$$C \alpha \frac{1}{d}$$

where α indicates a proportional relationship. Due to this proportional relationship, the capacitive sensing system is able to measure changes in capacitance and translate these changes into distance measurements.

For example, in one or more embodiments and as is known in capacitive proximity sensing circuits, the one or more electrodes 680 may be connected via a load resistor to an oscillating circuit including, for example, a sinusoidal wave generator. The amplitude and phase of the sinusoidal wave at the one or more electrodes 680 will be affected by the proximity of the diaphragm 614 to the one or more electrodes 680 (e.g., the capacitance increases as the electrodes move closer to the diaphragm 614 and the detected signal level decreases with increasing capacitance). In other words, the voltage level at the electrodes 680 will be proportional to 1/C as indicated above. A detector (e.g., a diode rectifier) may be used to convert the affected sinusoidal wave to a DC level which may then be operated on by a low pass filter. The detected signal level may be equated to distance and provided, for example, as a distance measurement output (e.g., a signal representative of the distance measurement that may be provided to a controller 625). However, other suitable sensing circuitry configurations may be used to capacitively sense position of the diaphragm.

The one or more electrodes 680 used to sense the position of the diaphragm 614 may be provided and/or positioned in a variety of manners. For example, such electrodes may be provided as a part of the receptacle used to mount the pressure pod apparatus 612 relative to system housing 655, may be provided as part of a port extending into the transducer side cavity 613, may be provided as part of the pressure pod apparatus 612 (e.g., coupled to or mounted adjacent thereto), may be provided adjacent to the base body portion of the pressure pod apparatus 612 (e.g., either as part of the pressure pod apparatus or at a location adjacent thereto).

Further, such one or more electrodes 680 may be provided in one or more different forms, such as a single electrode, multiple electrodes, or by an electrode pad. For example, an electrode pad may be used that provides a plurality of electrodes capable for use in providing capacitive measurements representative of the position of the diaphragm 614.

In one embodiment, the one or more electrodes 680 may be provided by an electrode pad adjacent the base section 658 of the base body portion 624 of the pressure pod apparatus 612 as shown in FIG. 9 (e.g., either as part of the connection apparatus 640 or the pressure pod apparatus 612). As such, when the diaphragm 614 is centered, the electrode pad is at a certain distance from the diaphragm 614 and is connectable to other processing components (e.g., amplifiers, control circuitry, etc.) via communication line 623. In one embodiment, the electrode pad and the diaphragm 614 lie along axis 639 of the pressure pod body 611, and the cross-sectional area of the electrode pad 680 orthogonal to the axis 639 is substantially the same as the cross-sectional area of the diaphragm 614 orthogonal to the axis 639. As used in this instance, substantially the same refers to a cross-sectional area that is within +/−10 to 20 percent of another cross-section area.

The electrode pad 680 may be protected from electrostatic discharges by covering the entire surface of the electrode pad 680 with a protective covering 698 (e.g., a covering formed of glass or polymer) as shown in FIG. 9. In one embodiment, the covering 698 may be of a thickness as low as 0.5 mm and as high as 6 mm. Further, in one embodiment, the protective covering 698 may have a high dielectric constant such that it has only a small effect on the capacitance. In one embodiment, the electrode pad 680 is entirely separated from the base body section 658 by the high dielectric material.

Figure 12:
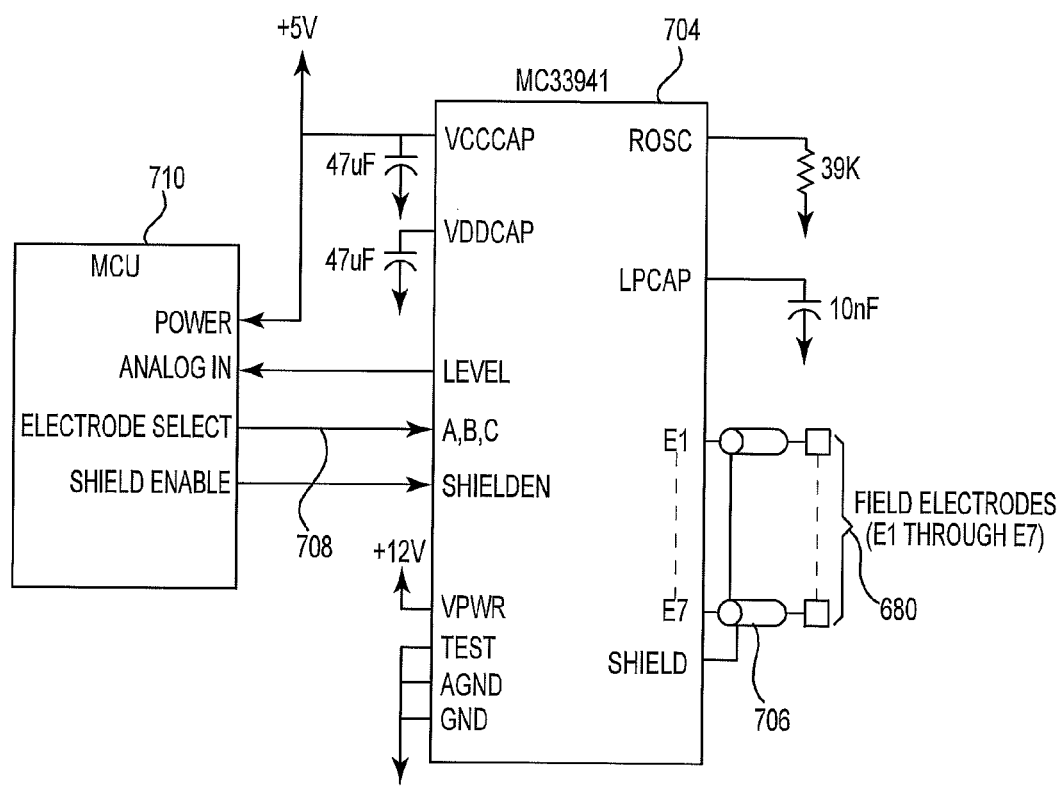
FIG. 12 is a schematic diagram for use in describing one exemplary implementation of a capacitive non-contact proximity sensor that may be used in a diaphragm repositioning system for repositioning a diaphragm of a pressure pod apparatus such as that shown generally in FIG. 9.

FIG. 12 is a schematic diagram for use in describing one exemplary implementation of a capacitive non-contact proximity sensor that may be used in a diaphragm repositioning system for repositioning a diaphragm 614 of a pressure pod apparatus 612 such as that shown generally in FIG. 9. For example, FIG. 12 shows an amplifier for a proximity sensor utilizing a simple electrode pad 680 and a ground plane as the proximity sensor. The MC33941 device 704 available from Freescale Semiconductor normally used for proximity sensing touch screens generates a low radio frequency sine wave with nominal 5.0 V peak-to-peak amplitude. The frequency may be set by an external resistor and optimized for 120 kHz. An internal multiplexer may route the signal to one of the seven (7) electrode terminals 706 under control of the ABC input terminals 708. A receiver multiplexer may be simultaneously connected to the selected electrode and route its signal to a detector, which converts the sine wave to a DC level. The DC level may be filtered by an external capacitor, multiplied and offset to increase sensitivity. All electrode outputs may be grounded internally by the device when not selected. The amplitude and phase of the sinusoidal wave at the electrodes may be affected by the diaphragm 614 in proximity thereto.

A "capacitor" is formed between the driving electrode (e.g., one of the electrodes of electrode pad 680) and the diaphragm 614, each forming a "plate" that holds the electric charge. The voltage measured is an inverse function of the capacitance between the electrode being measured, the surrounding electrodes, and other objects (including the diaphragm 614) in the electric field surrounding the electrode. Increasing capacitance results in a decreasing voltage. The value of the series resistor (e.g., 22 k ohm) is chosen to provide a near linear relationship at 120 kHz over a range of 10 pF to 70 pF. The electrode being measured may be selected by addressing three digital select lines (A,B,C) and the analog output from MC33941 is read by microcontroller unit (MCU) 710 (e.g., a system processor) via an analog to digital convertor (ADC) input thereof (e.g., which may be part of controller 625 as shown in FIG. 9). In other words, the controller 625 as shown in FIG. 9 (e.g., including control circuitry such as MCU 710) accesses electrode measurement data for processing thereof and generating a control signal based on the sensed position of the diaphragm 614. The diaphragm 614 may then be repositioned towards the centered measuring position based on the control signal.

Figure 11:
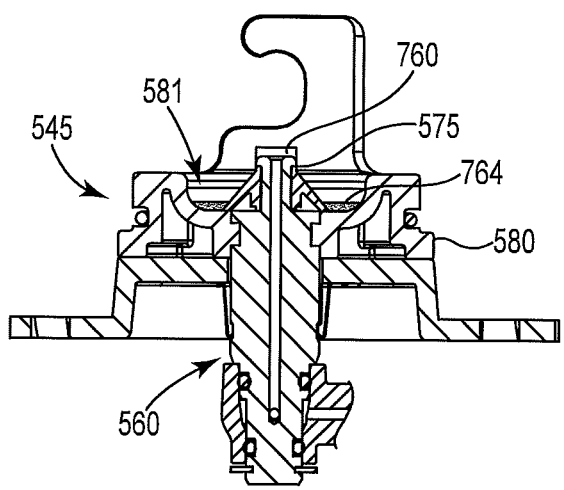
FIG. 11 shows a cross-section of another connection apparatus similar to that shown in FIG. 7C and including components for use in measuring position of a diaphragm of the pressure pod apparatus.

In another embodiment, the one or more electrodes 680 generally shown in FIG. 9 may be provided as shown in FIG. 11. For example, FIG. 11 shows connection apparatus 540 (previously described with reference to FIGS. 7A-7C). As shown in FIG. 11, one or more electrodes 760 may be provided at the first end region 575 of port 560 to be used as part of the capacitive proximity sensor (e.g., located a distance from the diaphragm when the pressure pod apparatus is mounted on the system housing to provide the capacitor of the sensor). Further, as shown in FIG. 11, one or more electrodes 764 may be provided in the receiving region 581 defined in the body portion 580 of receptacle 545 to be used as part of the capacitive proximity sensor (e.g., located a distance from the diaphragm when the pressure pod apparatus is mounted on the system housing to provide the capacitor of the sensor). For example, such electrodes may be both used as part of a capacitive proximity sensor or they may be used alone. In other words, only one of the electrodes may be needed to sense the position of the diaphragm (e.g., diaphragm 614).

Figure 10:
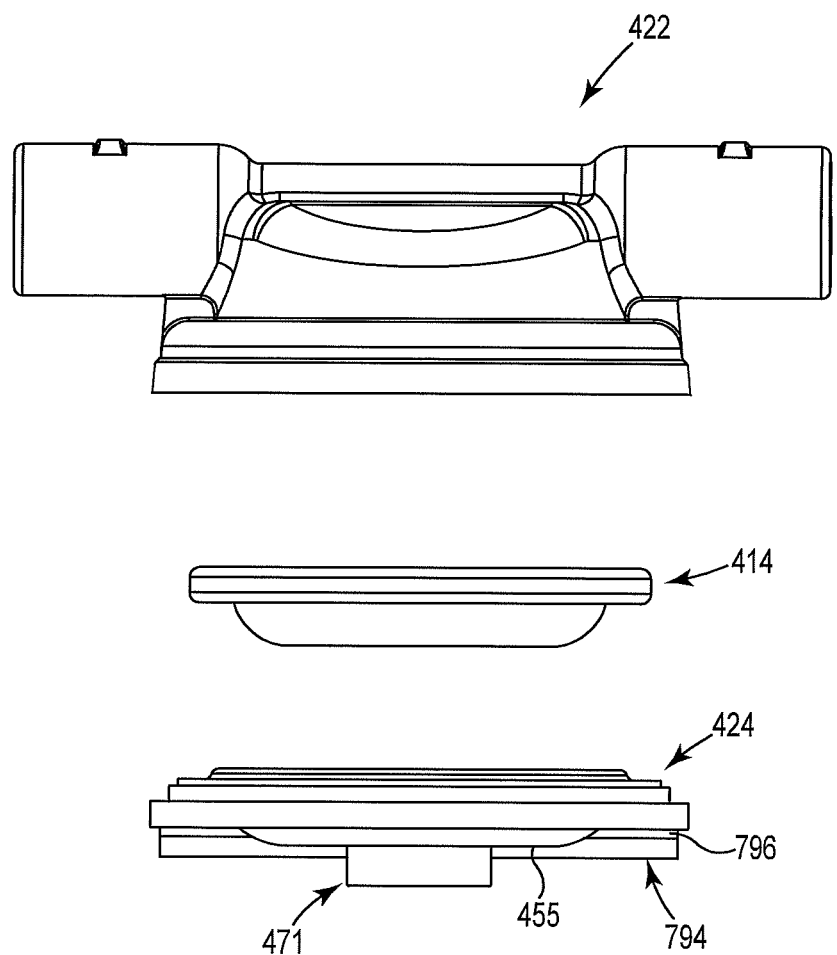
FIG. 10 shows a side view of an exemplary pressure pod apparatus that includes components for use in sensing position of a diaphragm of the pressure pod apparatus.

Still further, in one or more embodiments, the one or more electrodes 680 generally shown in FIG. 9 may be provided as shown in FIG. 10. For example, FIG. 10 shows one or more electrodes 794 as part of the pressure pod apparatus 412 (previously described with reference to FIGS. 6A-6C). As shown in FIG. 10, the one or more electrodes 794 may be provided adjacent to the surface 455 of the base body portion 424. For example, the one or more electrodes may be a single electrode, multiple electrodes, or an electrode pad such as described with reference to FIG. 9 to be used as part of the capacitive proximity sensor. Such electrodes may be coupled thereto in any suitable manner (e.g., using adhesives, mechanical fastening apparatus, etc.). The one or more electrodes 794 may be separated from the base body portion 424 by a dielectric material 796 (e.g., glass or polymer) as shown in FIG. 10. In one embodiment, the material 796 may be of a thickness as low as 0.5 mm and as high as 6 mm. Further, in one embodiment, the dielectric material 796 may have a high dielectric constant such that it has only a small effect on the capacitance. In one embodiment, the one or more electrodes 794 may be entirely separated from the base body portion 424 by the high dielectric material.

One will recognize that the one or more electrodes for use in the capacitive proximity sensor may be provided in any suitable manner. The various locations and types of electrodes described herein is not to be taken as limiting to the scope of the configurations of capacitive sensors capable of providing a diaphragm position signal for use in repositioning the diaphragm to a centered measuring position.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. An extracorporeal treatment system including a pressure measurement system comprising:
a pressure pod body comprising at least a pod body portion and a base body portion;
a diaphragm separating a liquid side cavity defined at least in part by the pod body portion from a transducer side cavity defined at least in part by the base body portion, wherein the liquid side cavity is in fluid communication with an inlet and an outlet, and further wherein the diaphragm is displaceable from a centered measuring position into the liquid side cavity towards the pod body portion and is displaceable from the centered measuring position into the transducer side cavity towards the base body portion;

a pressure transducer operatively coupled to the transducer side cavity such that pressure of liquid when present in the liquid side cavity is transferred to the transducer side cavity via the diaphragm and measureable by the pressure transducer;

a position sensor to sense the position of the diaphragm;

a controller operatively coupled to the position sensor to receive one or more signals representative of the position of the diaphragm and to generate a control signal based thereon for use in repositioning the diaphragm towards the centered measuring position; and pump apparatus operatively coupled to the controller and the transducer side cavity to reposition the diaphragm to the centered measuring position based on the control signal generated by the controller.

2. The system of claim 1, wherein the position sensor comprises at least one of an electro-optical proximity sensor and a capacitive proximity sensor.

3. The system of claim 1, wherein the system further comprises:

a system housing to contain at least the controller and the pressure transducer; and a connection apparatus to mount the pressure pod body on the system housing, wherein the connection apparatus comprises a port to connect the transducer side cavity to the pressure transducer contained in the system housing when the pressure pod body is mounted on the system housing by the connection apparatus, wherein the position sensor comprises a proximity sensor located to sense the position of the diaphragm when the pressure pod body is mounted on the system housing by the connection apparatus.

4. The system of claim 3, wherein the proximity sensor comprises an electro-optical proximity sensor comprising at least an optical transmitter device and an optical detector device mounted on the connection apparatus to sense the position of the diaphragm when the pressure pod body is mounted on the system housing by the connection apparatus.

5. The system of claim 3, wherein the proximity sensor comprises a capacitive proximity sensor comprising one or more electrodes located adjacent the base body portion of the pressure pod body when the pressure pod body is mounted on the system housing by the connection apparatus.

6. The system of claim 5, wherein the capacitive proximity sensor comprises one or more electrodes coupled to at least a portion of the base body portion.

7. The system of claim 3, wherein the proximity sensor comprises a capacitive proximity sensor comprising one or more electrodes provided proximate an end of the port located adjacent or within the transducer side cavity.

8. A pressure measurement method comprising:

providing a pressure pod body comprising at least a pod body portion and a base body portion, wherein a diaphragm separates a liquid side cavity defined at least in part by the pod body portion from a transducer side cavity defined at least in part by the base body portion, wherein the liquid side cavity is in fluid communication with an inlet and an outlet, and further wherein the diaphragm is displaceable from a centered measuring position into the liquid side cavity towards the pod body portion and is displaceable from the centered measuring position into the transducer side cavity towards the base body portion;

sensing pressure of a liquid in the liquid side cavity between the inlet and the outlet, wherein the pressure of liquid when present in the liquid side cavity is transferred to the transducer side cavity via the diaphragm;

sensing the position of the diaphragm;

generating a control signal based on the sensed position of the diaphragm; and repositioning the diaphragm towards the centered measuring position based on the control signal.

9. The method of claim 8, wherein generating a control signal based on the sensed position of the diaphragm comprises:

setting a predetermined range of acceptable diaphragm positions for sensing pressure;

comparing the sensed position of the diaphragm to the predetermined range; and generating a control signal based on the comparison.

10. The method of claim 8, wherein sensing the position of the diaphragm comprises sensing the position of the diaphragm at multiple times over multiple rotations of a pump providing for flow of the liquid through the liquid side cavity from inlet to outlet and averaging the sensed position of the diaphragm at the multiple times.

11. The method of claim 8, wherein repositioning the diaphragm towards the centered measuring position comprises providing gas to or removing gas from the transducer side cavity.

12. The method of claim 8, wherein sensing the position of the diaphragm comprises using a proximity sensor to sense the position of the diaphragm, wherein the proximity sensor comprises at least one of an electro-optical proximity sensor and a capacitive proximity sensor.

13. The method of claim 8, wherein the method further comprises:

providing a system housing to contain at least a controller to generate the control signal and a pressure transducer to sense pressure of the liquid in the liquid side cavity;

providing a connection apparatus to mount the pressure pod body on the system housing, wherein the connection apparatus comprises a port to connect the transducer side cavity to the pressure transducer contained in the system housing when the pressure pod body is mounted on the system housing by the connection apparatus;

mounting the pressure pod body on the system housing; and using a proximity sensor to sense the position of the diaphragm when the pressure pod body is mounted on the system housing by the connection apparatus.

14. The method of claim 13, wherein the proximity sensor comprises at least one of a capacitive proximity sensor comprising one or more electrodes coupled to at least a portion of the base body portion, a capacitive proximity sensor comprising one or more electrodes provided proximate an end of the port located adjacent or within the transducer side cavity, a capacitive proximity sensor comprising an electrode pad positioned adjacent the base body portion to sense the position of the diaphragm, and an electro-optical proximity sensor comprising an optical transmitter device and an optical detector device mounted on the connection apparatus.

15. A pressure measurement apparatus to be operatively mounted by a connection apparatus on a system housing of an extracorporeal treatment system, wherein the system housing contains a pressure transducer therein, the pressure measurement apparatus comprising:

a pressure pod body configured to be mounted on the system housing by the connection apparatus, wherein the pressure pod body comprises at least a pod body portion and a base body portion;

a diaphragm separating a liquid side cavity defined at least in part by the pod body portion from a transducer side cavity defined at least in part by the base body portion, wherein the liquid side cavity is in fluid communication with an inlet and an outlet, wherein the transducer side cavity is connectable to the pressure transducer such that pressure of liquid when present in the liquid side cavity is transferred to the transducer side cavity via the diaphragm and measureable by the pressure transducer, and further wherein the diaphragm is displaceable from a centered measuring position into the liquid side cavity towards the pod body portion and is displaceable from the centered measuring position into the transducer side cavity towards the base body portion; and a position sensor positioned adjacent the base body portion usable to sense the position of the diaphragm.

16. The apparatus of claim 15, wherein the position sensor comprises a proximity sensor, wherein the proximity sensor comprises one or more electrodes adjacent the base body portion.

17. The apparatus of claim 16, wherein the one or more electrodes are separated from the base body portion by a high dielectric material.

18. The apparatus of claim 16, wherein the proximity sensor comprises an electrode pad, and further wherein the electrode pad is entirely separated from the base body portion by the high dielectric material.

19. The apparatus of claim 16, wherein the proximity sensor comprises an electrode pad, wherein the electrode pad and the diaphragm lie along an axis of the pressure pod body, and further wherein the cross-sectional area of the electrode pad orthogonal to the axis is substantially the same as the cross-sectional area of the diaphragm orthogonal to the axis.

20. The system of claim 1, wherein the pressure pod body is provided as part of a disposable extracorporeal blood set.

* * * * *